United States Patent [19]
Golub et al.

[11] Patent Number: 6,100,248
[45] Date of Patent: Aug. 8, 2000

[54] METHOD OF INHIBITING CANCER GROWTH

[76] Inventors: Lorne M. Golub, 29 Whitney Gate, Smithtown, N.Y. 11787; Thomas F. McNamara, Box 44, Port Jefferson, N.Y. 11777; Nungavaram S. Ramamurthy, 10 Lynam Ct., Smithtown, N.Y. 11787; Hsi-Ming Lee, 20 Allyson Pl., Setauket, N.Y. 11733; Sanford Simon, 71 Cedar St., Stony Brook, N.Y. 11790; Balakrishna L. Lokeshwar, 12615 SW. 112 Ct., Miami, Fla. 33176; Marie G. Selzer, 6035 Bayview Dr., Fort Lauderdale, Fla. 33308; Norman L. Block, 19000 SW. 72nd Ave., Miami, Fla. 33156

[21] Appl. No.: 09/007,645

[22] Filed: Jan. 15, 1998

Related U.S. Application Data

[63] Continuation-in-part of application No. 08/783,655, Jan. 15, 1997, Pat. No. 5,837,696.

[51] Int. Cl.⁷ ..................................................... A01N 37/18
[52] U.S. Cl. ........................... 514/152; 514/153; 514/154
[58] Field of Search ..................... 514/152, 154, 514/153; 435/7.23

[56] References Cited

U.S. PATENT DOCUMENTS

| | | | |
|---|---|---|---|
| 5,308,839 | 5/1994 | Golub et al. | 514/152 |
| 5,321,017 | 6/1994 | Golub et al. | 514/152 |
| 5,563,130 | 10/1996 | Backer | 514/152 |
| 5,567,693 | 10/1996 | Backer et al. | 514/154 |
| 5,574,026 | 11/1996 | Backer et al. | 514/152 |
| 5,668,122 | 9/1997 | Fife et al. | 514/152 |
| 5,837,696 | 11/1998 | Golub et al. | 514/152 |

FOREIGN PATENT DOCUMENTS

92/12717  8/1992  WIPO.

OTHER PUBLICATIONS

Basset P, Okada A, Chenard M–P, Kannan R, Stoll I, Anglard P, Bellocq J–P, Rio M–C, "Matrix Metalloproteinases as Stromal Effectors of Human Carcinoma Progression: Therapeutic Implications", *Matrix Biology* 15:535–541 (1997).

Golub LM, Ramamurthy NS, Leungt M, McNamara TF, "Low–Dose Doxycycline Therapy: Effect on Gingival and Crevicular Fluid Collagenase Activity in Humans", *J. Periodont Res* 25: 321–330 (1990).

Golub LM, Lee HM, Lehrer G, Nemiroff A, McNamara TF, Kaplan R, Ramamurthy NS, "Minocycline Reduces Gingival Collagenolytic Activity During Diagetes", *Journal of Periodontal Research* 18:516–526 (1983).

Hatsu M, Sasaki T, Watabe H–O, Miyadoh S, Nagasawa M. Shomura T, Sezaki M, Inouye S, Kondo S, "A New Tetracycline Antibiotic with Antitumor Activity", *The Journal of Antibiotics* 45(3):320–324 (1992).

Hatsu M, Sasaki T, Gomi S, Kodama Y, Sezaki M, Inouye S, Kondo S, "A New Tetracycline Antibiotic with Antitimor Activity", *The Journal of Antibiotics* 45(3):325–330 (1992).

Johnson RK, Goldin A, "The Clinical Impact of Screening and Other Experimental Tumor Studies", *Cancer Treatment Reviews* 2:1–31 (1975).

Johnson et al., "Cancer Treatment Reviews", 2:1 (1975).

Okada A, Bellocq J–P, Rouyer N, Chenard M–P, Rio M–C, Chambron P, Basset P, "Membrane–Type Matrix Metalloproteinase (MT–MMP) Gene is Expressed in Stromal Cells of Human Colon, Breast, and Head and Neck Carcinoma", *Proc. Natl. Acad. Sci. USA* 92:2730–2734 (1995).

Okada A, Tomasetto C, Lutz Y, Bellocq J–P, Rio M–C, Basset P, "Expression of Matrix Metalloproteinases During Rat Skin Wound Healing: Evidence that Membrane Type–1 Matrix Metalloproteinase is a Stromal Activator of Pro–Gelatinase A", *The Journal of Cell Biology* 137(1):67–77 (1997).

Sotomayor EA, Teicher BA, Schwartz GN, Holden SA, Menon K, Herman TS, Frei III E, Minocycline in Combination with Chemotherapy or Radiation Therapy in Vitro and in Vivo, *Cancer Chemother Pharmacol* 30:377–384 (1992).

Uitto V–J, Firth JD, Nip L, Golub LM "Doxycycline and Chemically Modified Tetracyclines Inhibit Gelatinase A (MMP–2) Gene Expression in Human Skin Keratinocytes", *Annals of the New York Academy of Sciences* 732:140–151 (1994).

Zeng ZS, Huang Y, Cohen AM, Guillem JG, "Prediction of Colorectal Cancer Relapse and Survival via Tissue RNA Levels of Matrix Metalloproteinase–9", *Journal of Clinical Oncology* 14(12):3133–3140 (1996).

Zucker S, Lysik RM, Ramamurthy NS, Golub LM, Wieman JM, Wilkie DP, "Diversity of Melanoma Plasma Membrane Proteinases: Inhibition of Collagenolytic and Cytolytic Activites by Minocycline", *JNCI* 75(3):517–525 (1985).

Zucker S, Turpeenniemi–Hujanen, T, Ramamurthy N, Wieman J, Lysik R, Gorevic P, Liotta LA, Simon SR, Golub LB, "Purification and Chracterization of a Connective–Tissue–Degrading Metalloproteinase from the Cytosol of Metastatic Melanoma Cells", *Biochem. J* 245:429–437 (1987).

Zucker S, Wieman J, Lysik RM, Imhof B, Nagase H, Ramamurthy N, Liotta LA, Golub LM, "Gelatin–Degrading Type IV Collagenase Isolated from Human Small Cell Lung Cancer", *Invasion Metastasis* 9:167–181 (1989).

Lokeshwar et al, Proc. of the American Assn. for Cancer Research Annual Meeting vol. 38 pp. 428 (abstract only), Apr. 1997.

*Primary Examiner*—Sheela Huff
*Attorney, Agent, or Firm*—Hoffmann & Baron, LLP

[57] ABSTRACT

The invention is a method of inhibiting cancer growth, by inhibiting cellular proliferation, invasiveness, or metastasis, or by inducing cytotoxicity against cancer in mammals. The method employs 6-demethyl-6-deoxy-4-de(dimethylamino) tetracycline (CMT-3) and other functionally related chemically modified, preferably non-antibacterial, tetracycline compounds to inhibit cancer growth. The method is particularly effective to inhibit the establishment, growth, and metastasis of solid tumors, such as tumors derived from colon cancer cells, breast cancer cells, melanoma cells, prostatic carcinoma cells, or lung cancer cells.

34 Claims, 21 Drawing Sheets

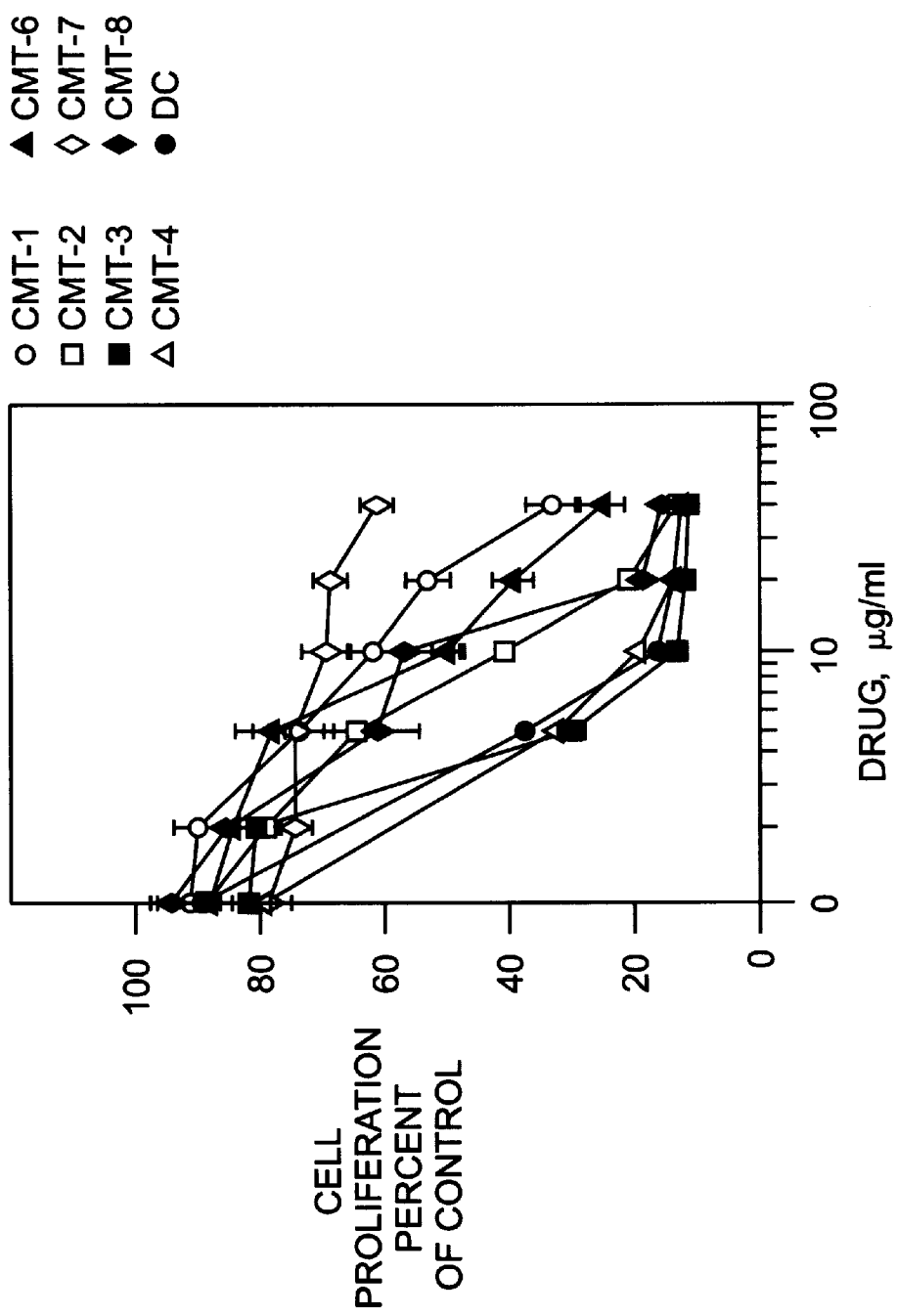
FIG-2A LNCaP

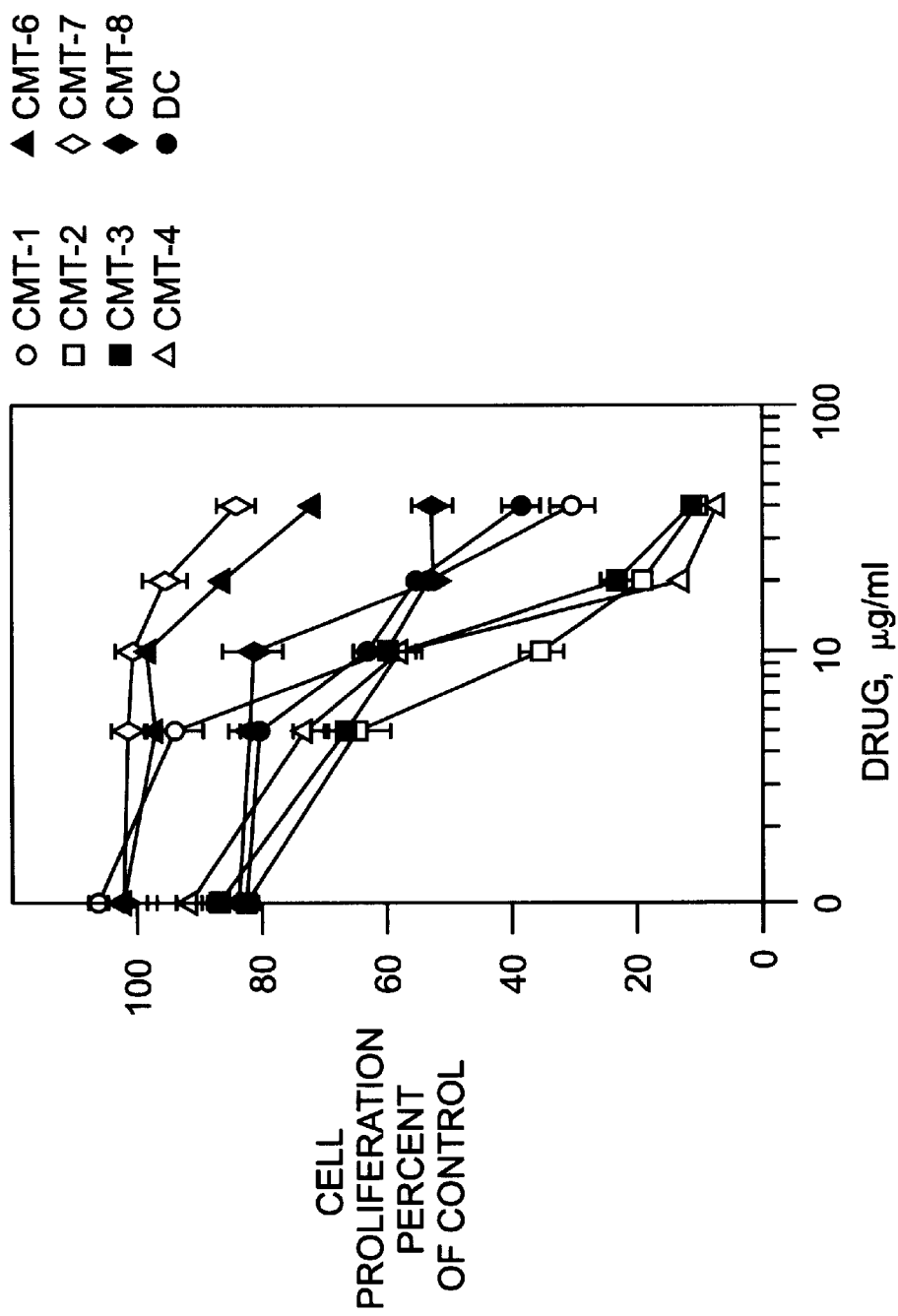
FIG-2B TSU PR1

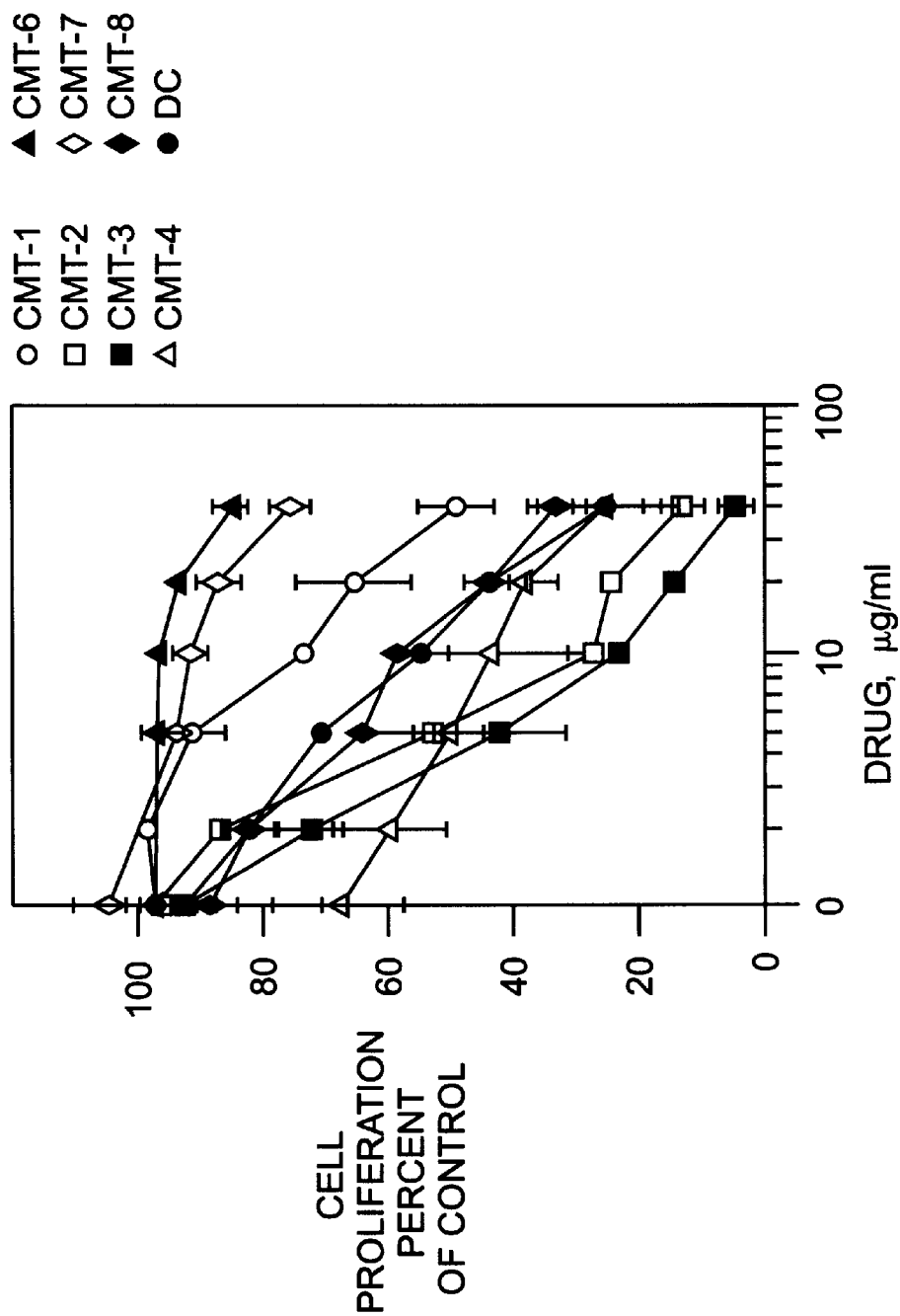
FIG-2C  MAT LyLu

FIG-3A DU145
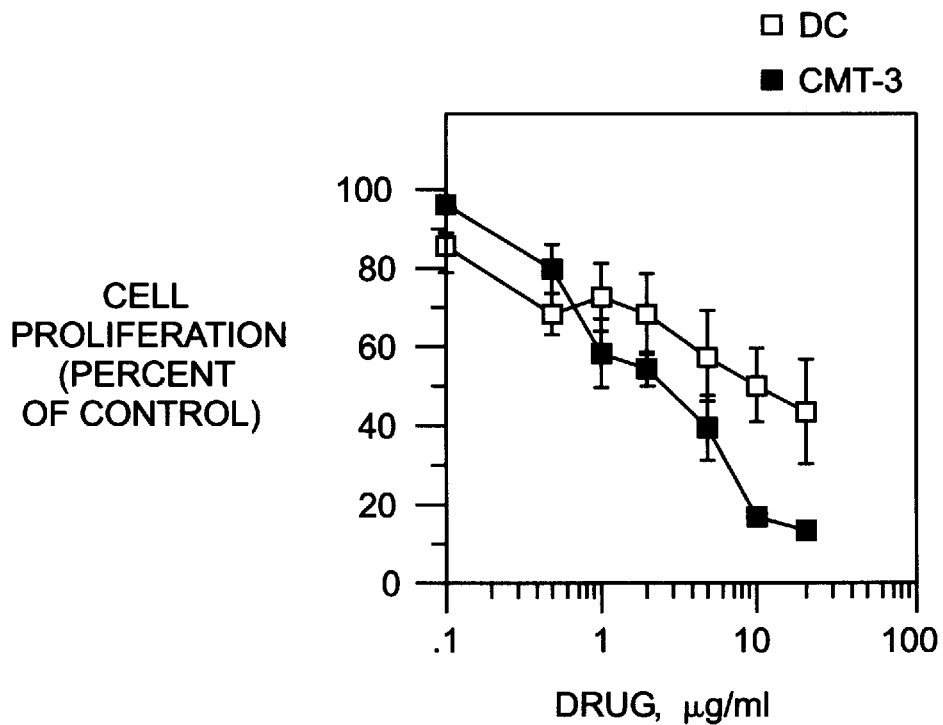
FIG-3B PC-3
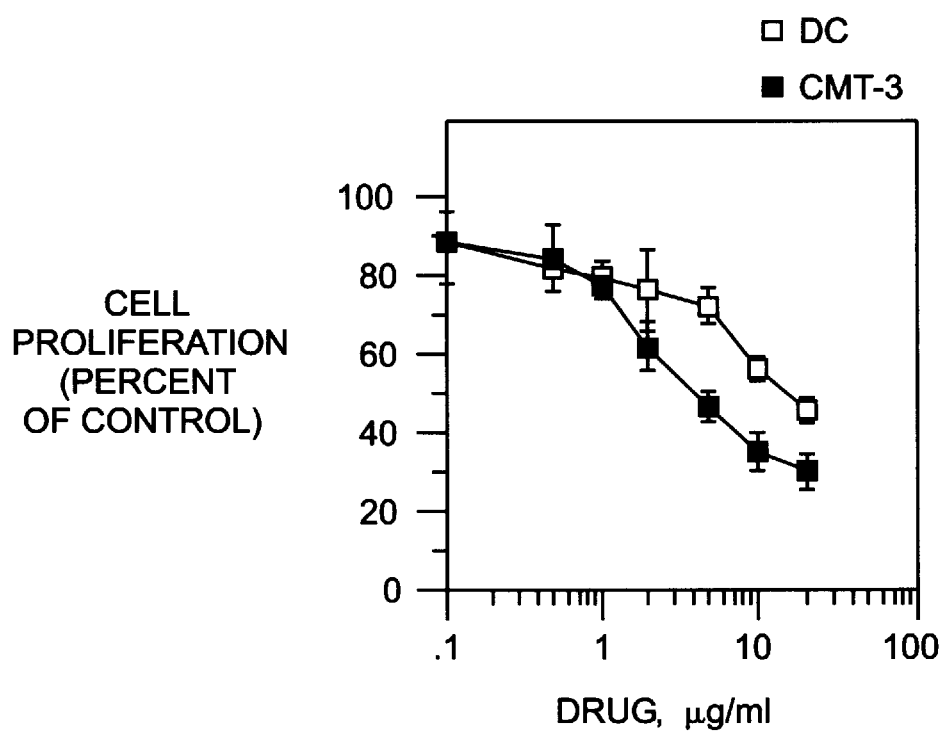

FIG-3C BPH-1
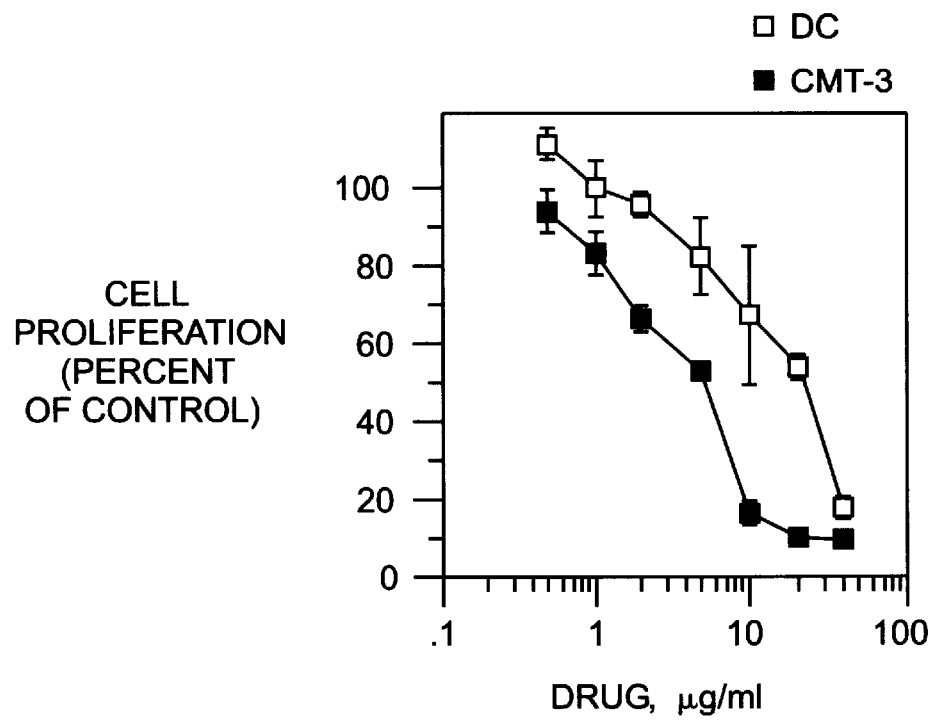
FIG-3D FHS733
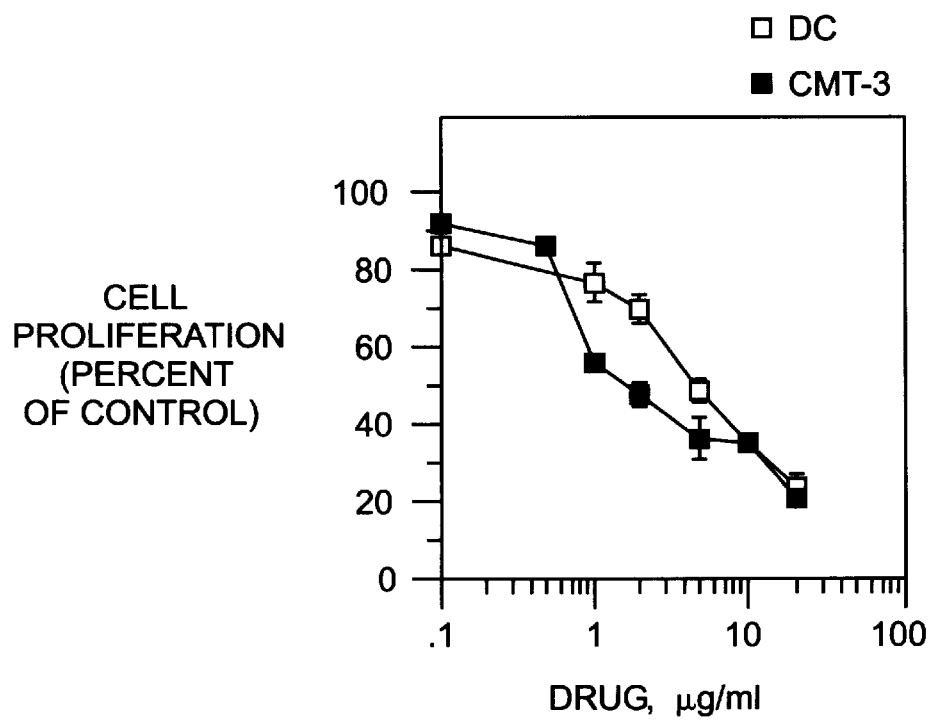

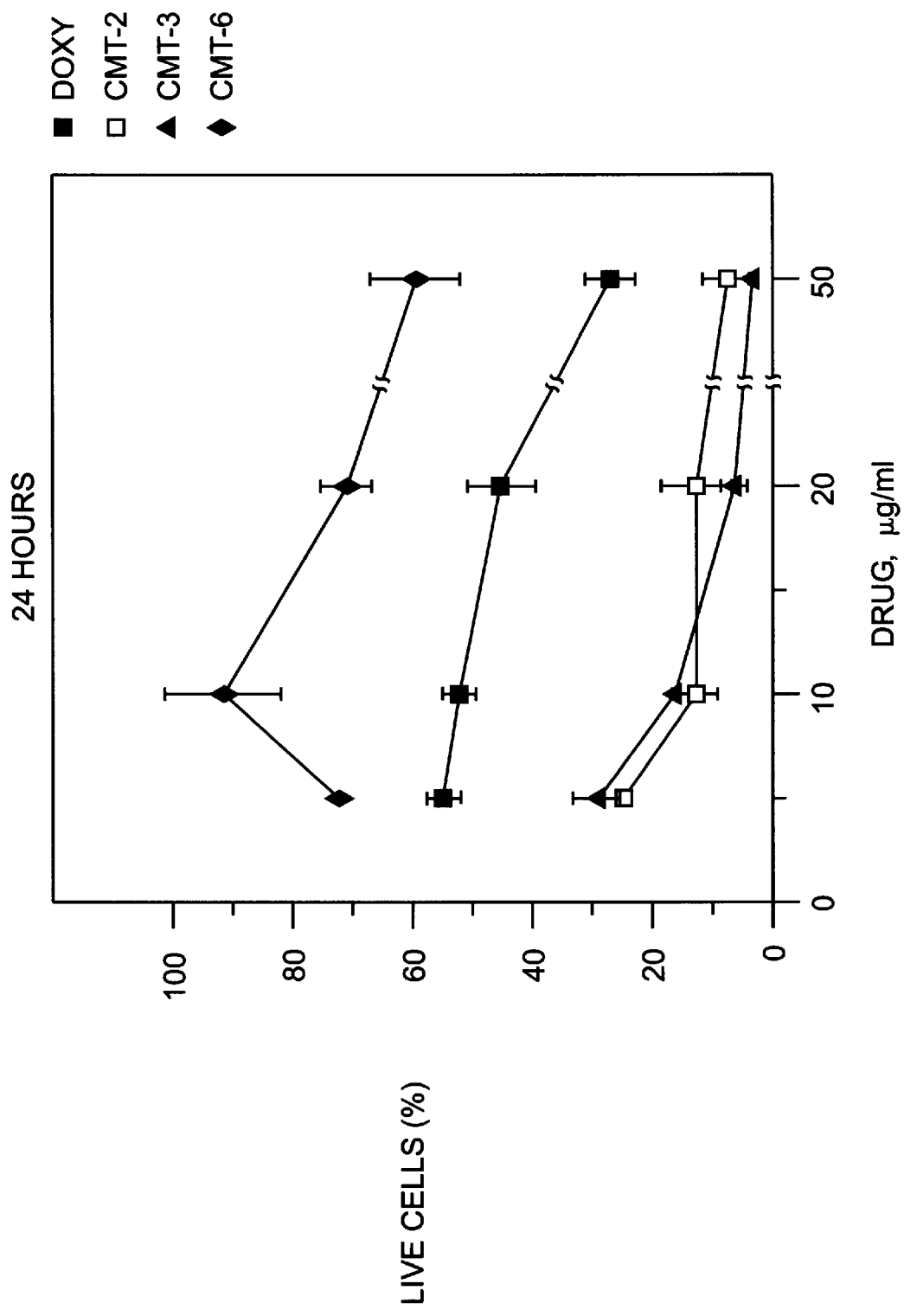
FIG-4A CYTOTOXICITY OF CMTS

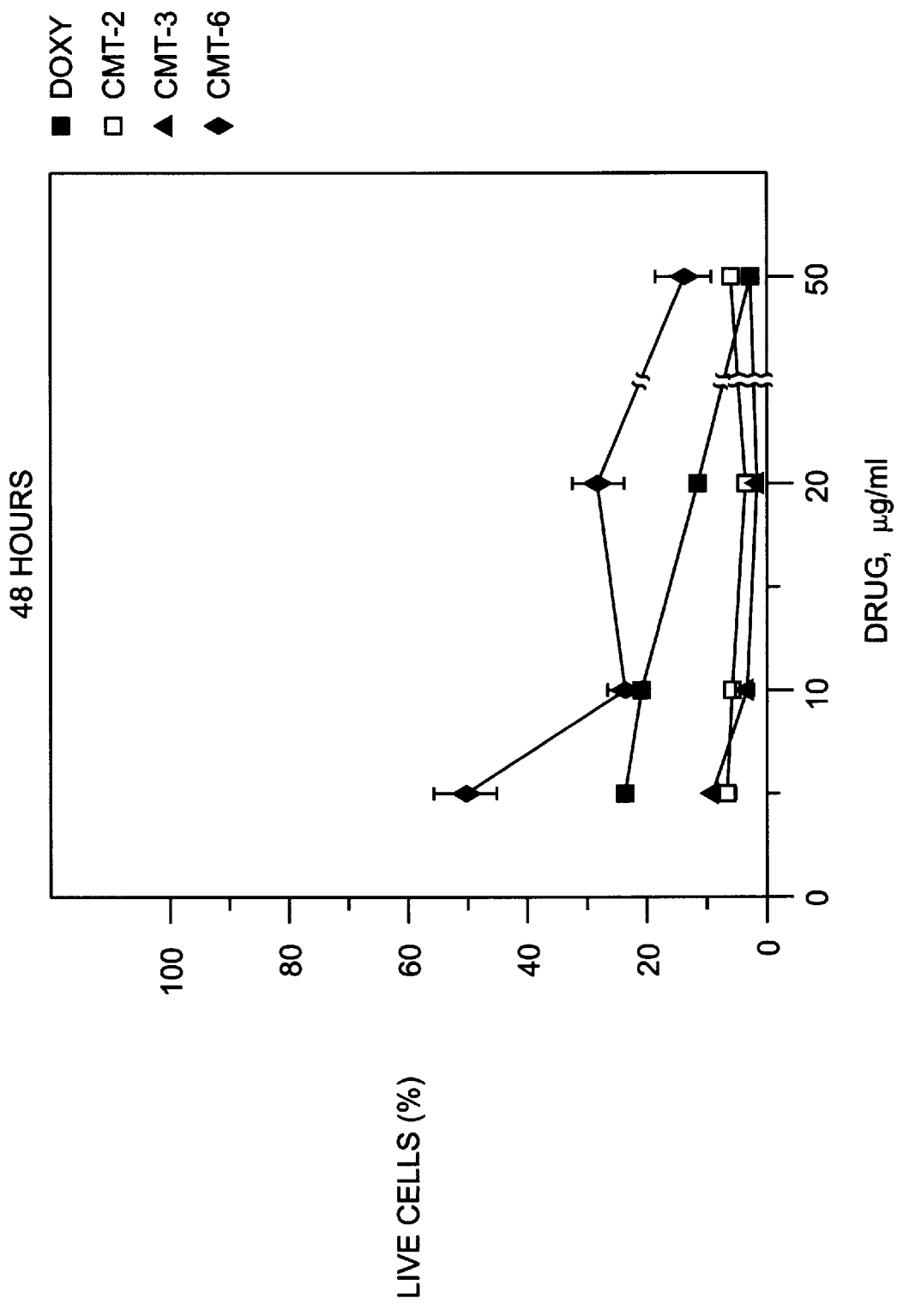
FIG-4B CYTOTOXICITY OF CMTS

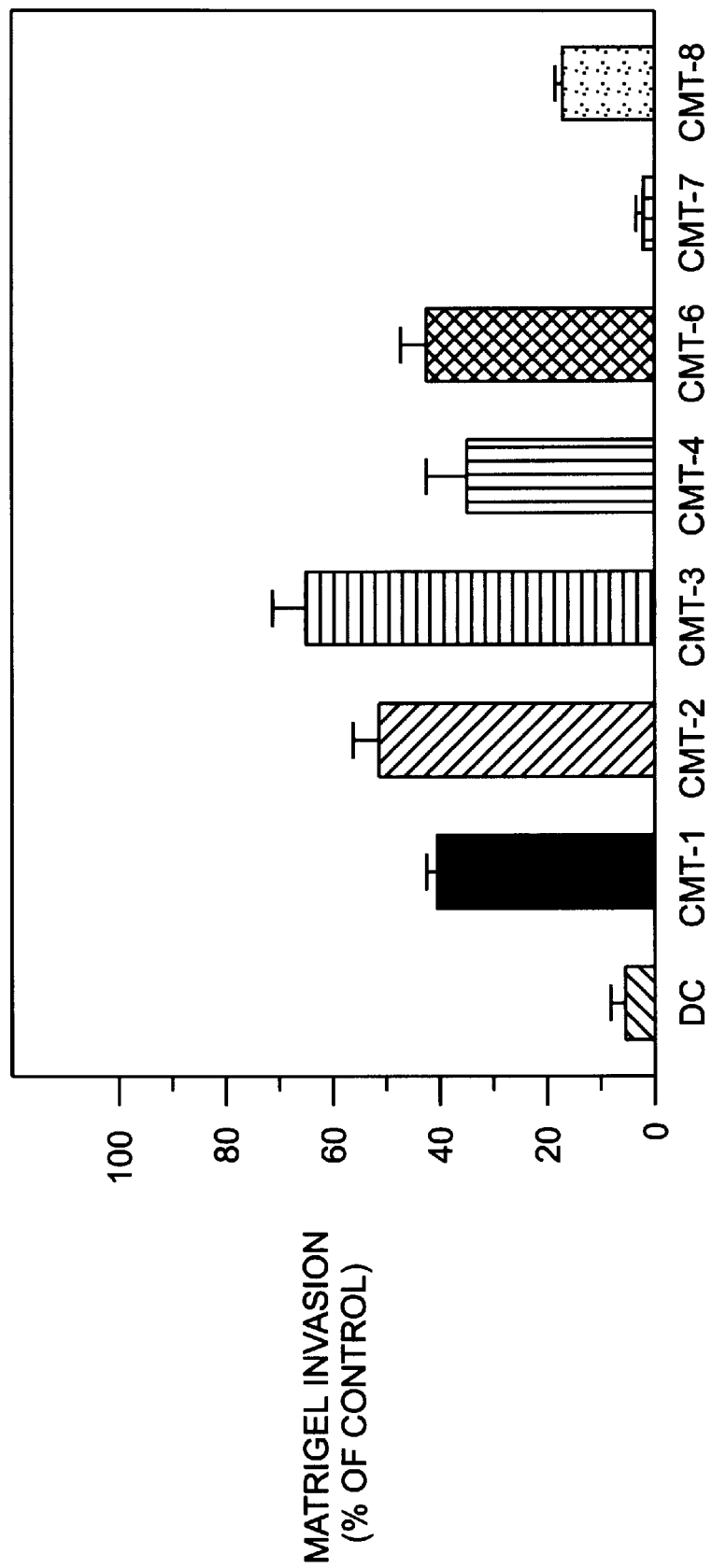

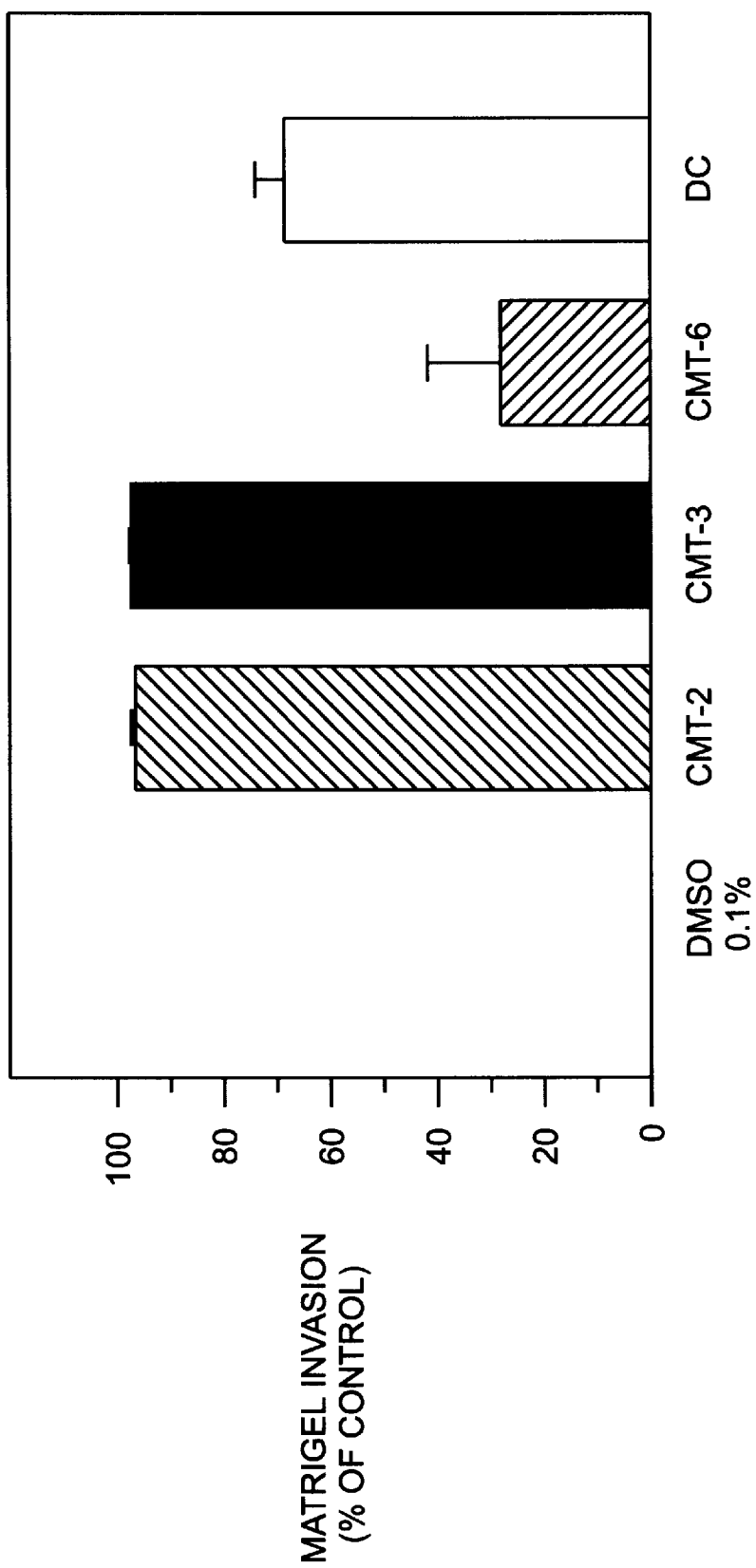
FIG-5B MAT LyLu

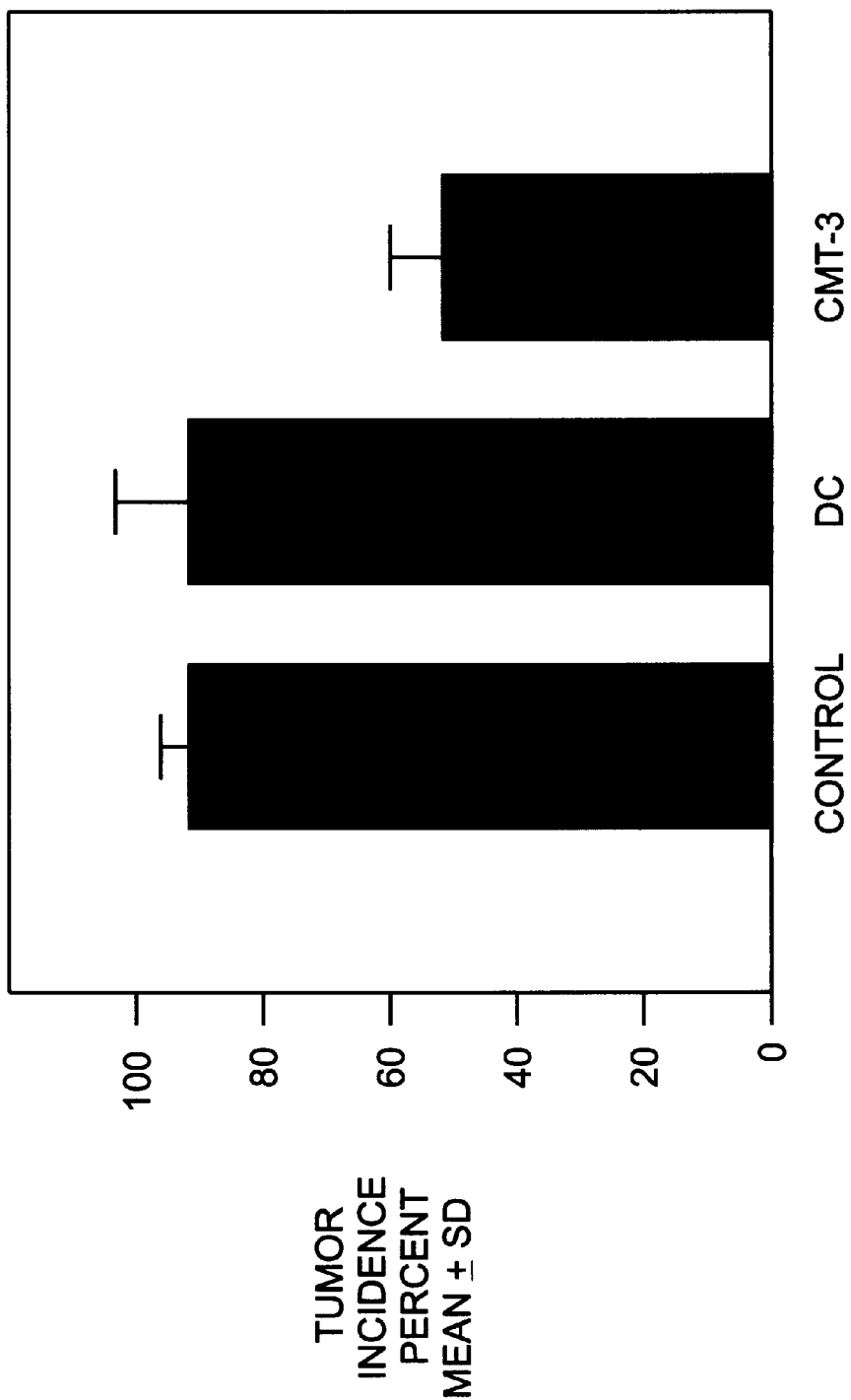
FIG-7A TUMOR INCIDENCE

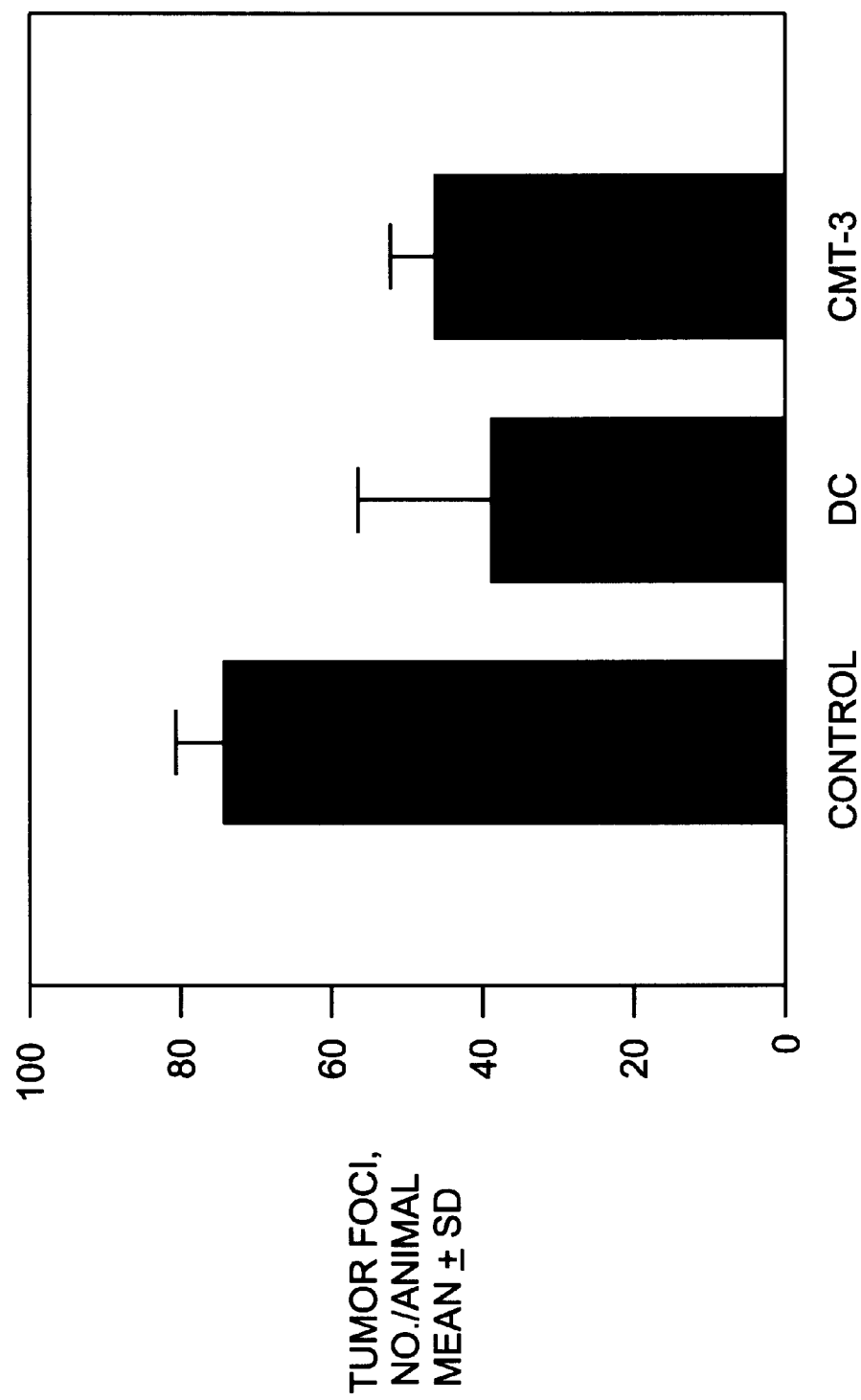
FIG-7B METASTASIS

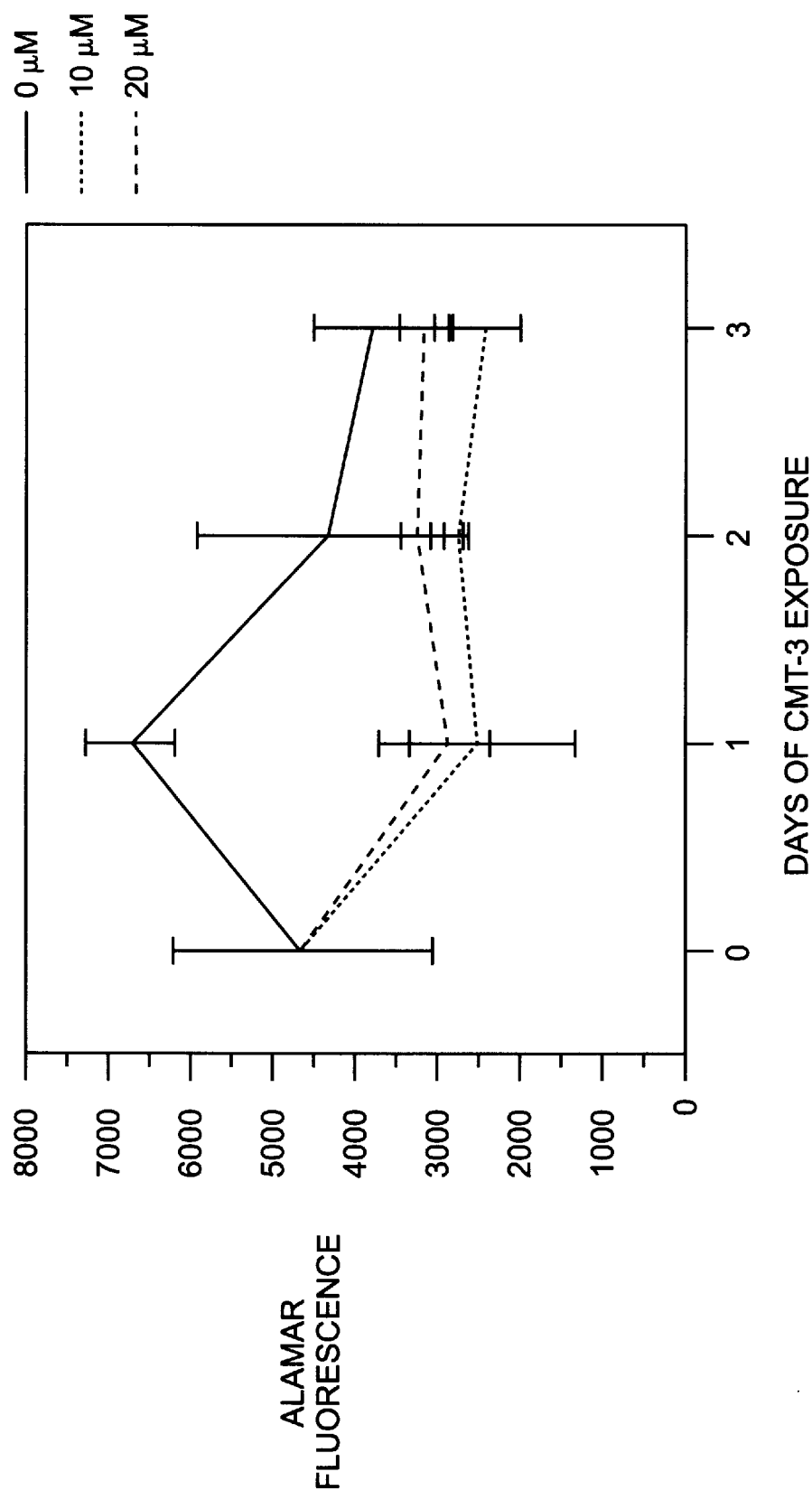
FIG-9A EFFECTS OF CMT-3 OVER 3 DAYS
PROSTATE STROMAL CELLS: 37 YEAR OLD, CMT-3: 0, 10 AND 20 μM

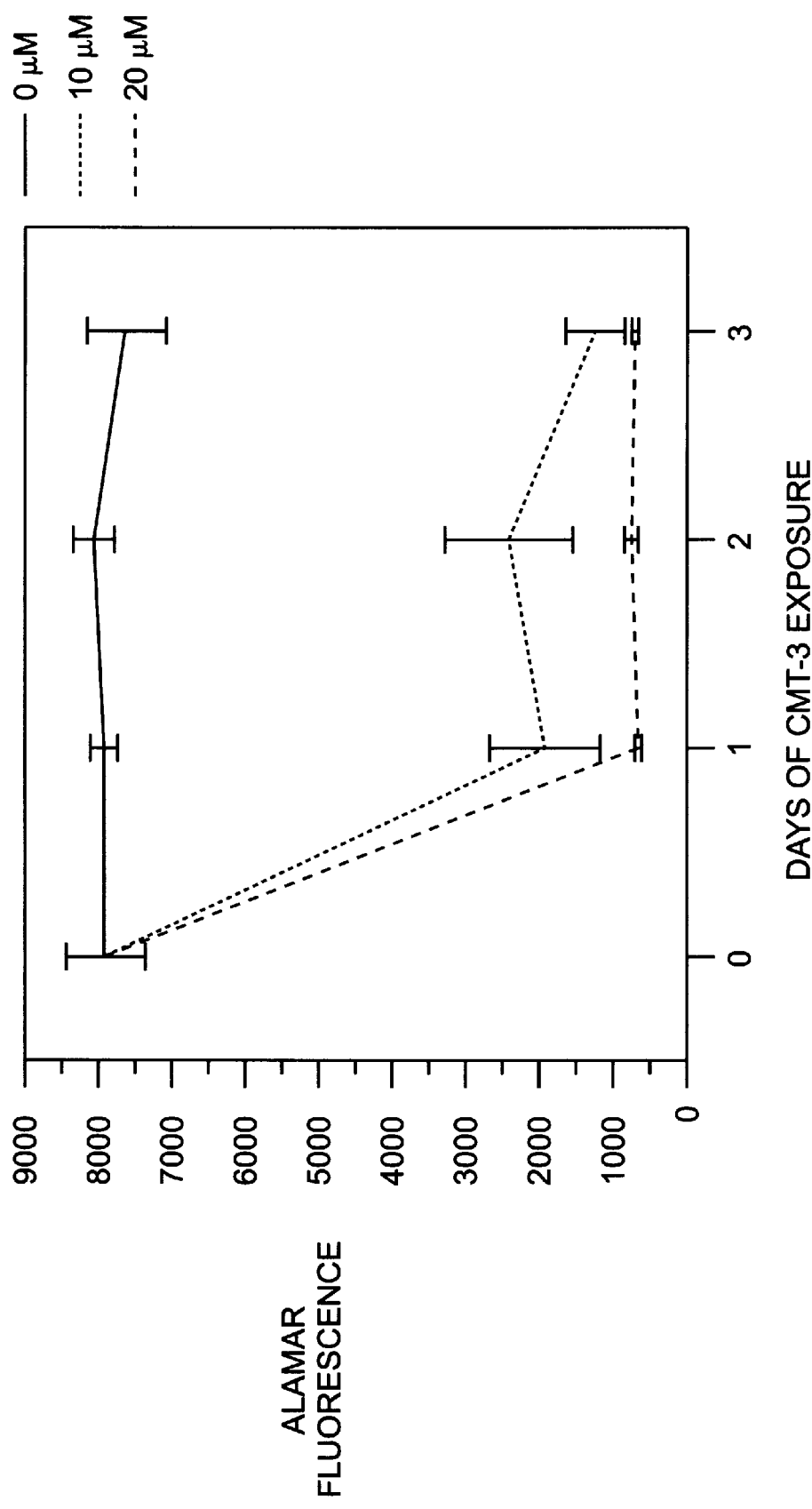
FIG-9B EFFECTS OF CMT-3 OVER 3 DAYS
PROSTATE TUMOR: LnCap CMT-3: 0, 10 AND 20 μM

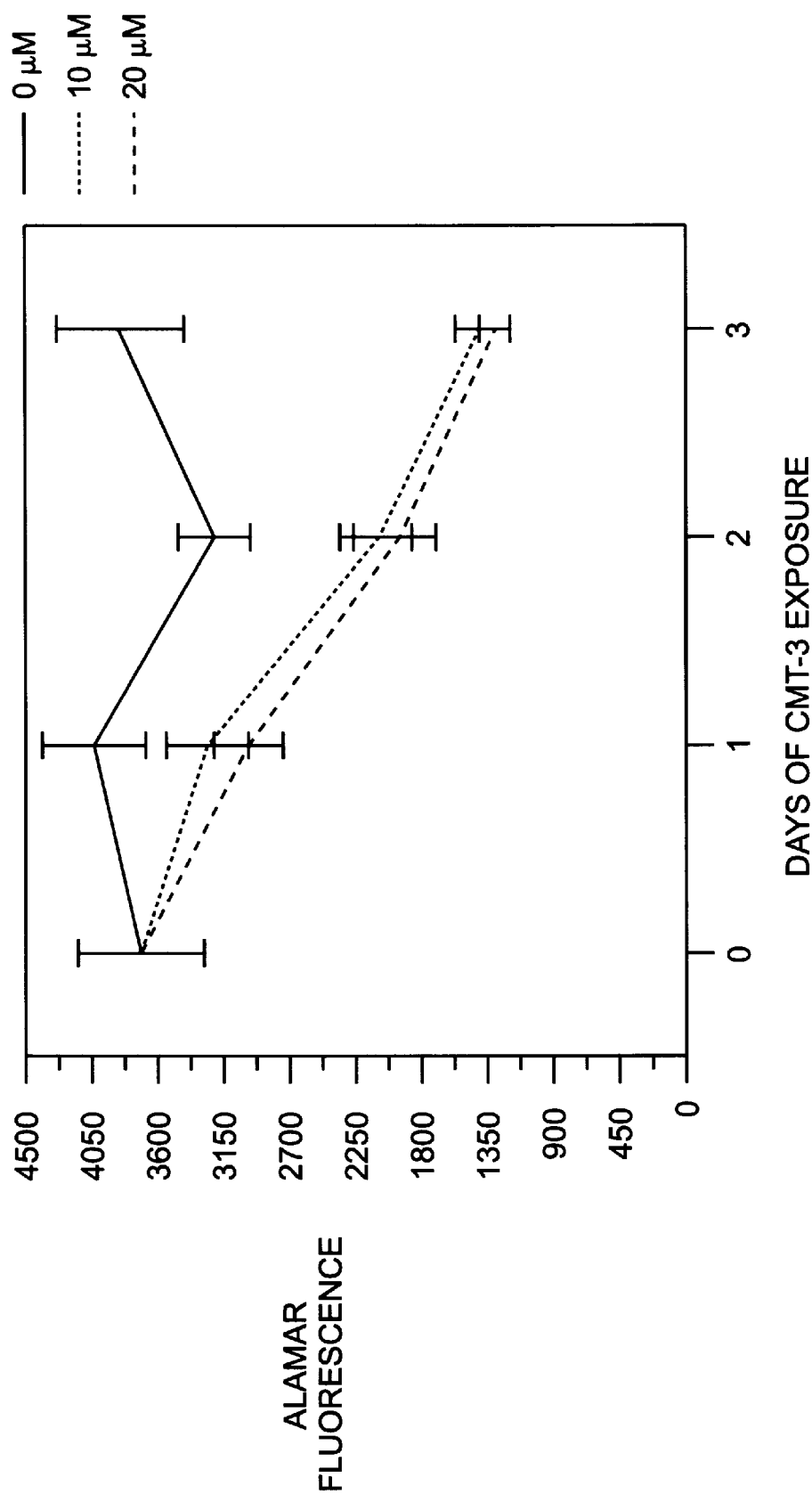

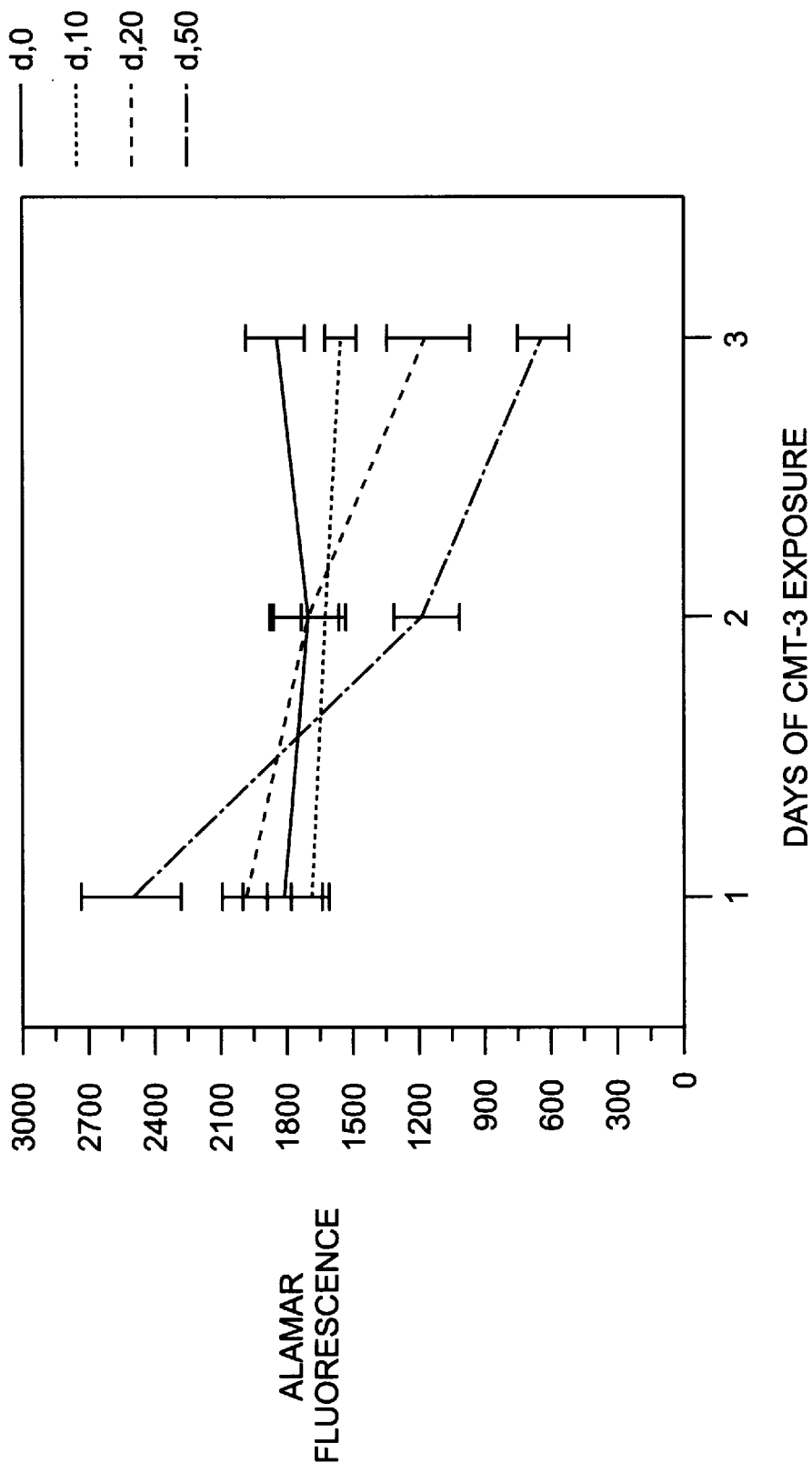
FIG-9D EFFECTS OF CMT-3 OVER 3 DAYS
PROSTATE TUMOR: DU-145, CMT-3: 0, 10, 20, AND 50 µM

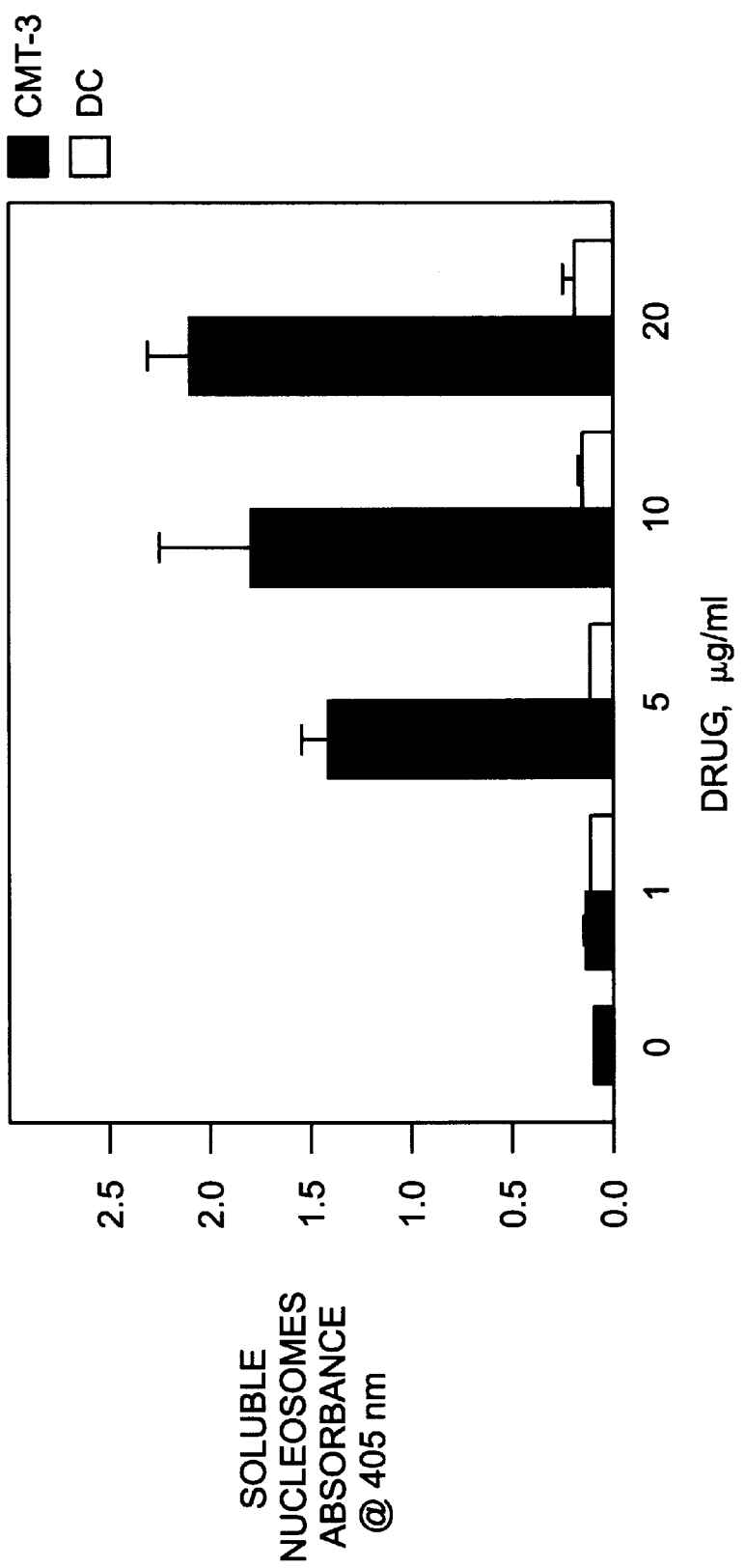
FIG-10A CMT-3 INDUCED APOPTOSIS

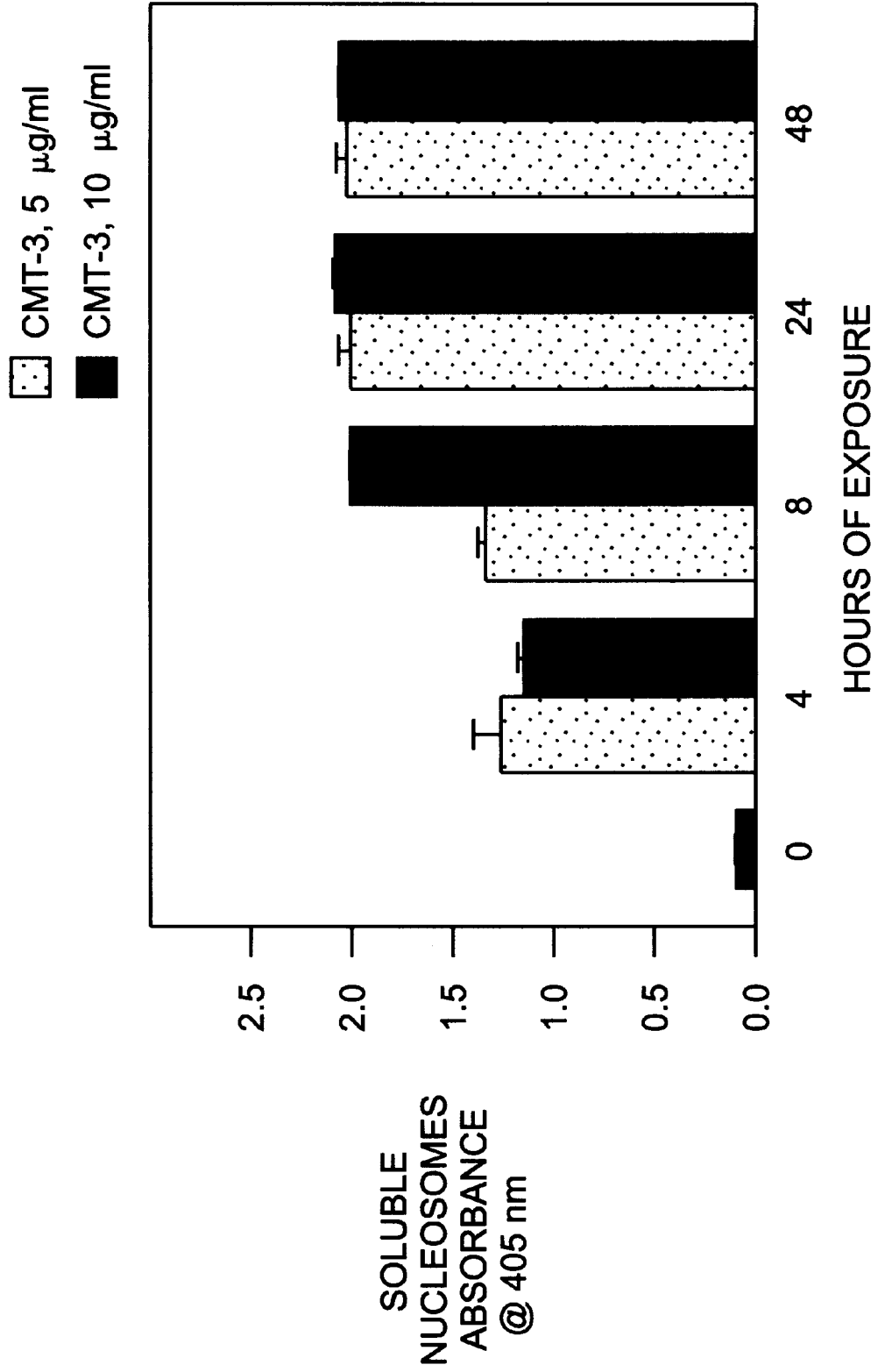
FIG-10B  CMT-3 INDUCED APOPTOSIS

METHOD OF INHIBITING CANCER GROWTH

This is a continuation-in-part of U.S. application Ser. No. 08/783,655, filed on Jan. 15, 1997 now U.S. Pat. No. 5,837,696.

This invention was made with Government support under Grant No. R37-DE03987 awarded by the National Institutes of Health through the National Institute of Dental Research and Grant No. R29-CA61038 awarded by the National Institutes of Health. The Government has certain rights in the invention.

BACKGROUND OF THE INVENTION

The invention relates to methods of reducing cancer growth in biological systems. More specifically, the invention relates to the inhibition of solid tumor invasiveness and metastasis in mammals.

Cancer, in all of its myriad manifestations, remains a devastating scourge upon mankind. While progress in preventing and treating cancer has been made, including particular success against Hodgkin's lymphoma and certain other forms, many types of cancer remain substantially impervious to prevailing treatment protocols. Typically, cancer is treated by chemotherapy, in which highly toxic chemicals are given to the patient, or by radiotherapy, in which toxic doses of radiation are directed at the patient. While commonly effective to kill huge numbers of cancer cells, these "cytotoxic" treatments also kill extraordinary numbers of healthy cells, causing the patient to experience acute debilitating symptoms including nausea, diarrhea, hypersensitivity to light, hair loss, etc. The side effects of these cytotoxic compounds limits the frequency and dosage at which they can be administered. Such disabling side effects can be mitigated to some degree by using compounds that selectively target cycling cells, i.e., interfering with DNA replication or other growth processes in cells that are actively reproducing. Since cancer cells are characterized by their extraordinary ability to proliferate, such protocols preferentially kill a larger proportion of cancer cells in comparison to healthy cells, but cytotoxicity and ancillary sickness remains a problem.

Other more recent developments include efforts to develop monoclonal antibodies specific for oncogenes or HLA specificities, to identify cancer cells with great precision. However, these procedures are very expensive and extremely procedurally elaborate, yet still fail to produce the desired efficacy. Indeed, such procedures have been reported to be effective in only a small subpopulation of treated patients.

The area of cancer research concerned with the mechanisms of tumor cell invasion has benefited greatly from the conceptual framework proposed by Liotta and colleagues (see, e.g., Yamamoto et al. (1996); Emmert-Buck et al. (1994). This model describes the invasive process as a logical progression of events involving three discernible stages: attachment of tumor cells to an extracellular matrix (ECM), proteolytic digestion of the matrix, and movement of cells through the proteolytically degraded barrier. A key factor in this process is the regulation of the matrix metalloproteinases (MMPs; including gelatinases A and B; MMP-2 and MMP-9, respectively, and MMP-3 (Lokeshwar et al. 1993a)), that play a major role in the degradation of the ECM during invasion.

Tetracycline and a number of its chemical relatives form a particularly successful class of antibiotics. Certain of the tetracycline compounds, including tetracycline itself, as well as sporocycline, etc., are broad spectrum antibiotics, having utility against a wide variety of bacteria. The parent compound, tetracycline, has the following general structure:

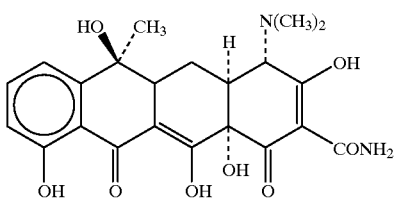

The numbering system for the multiple ring nucleus is as follows:

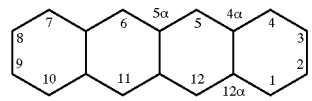

Tetracycline, as well as the 5-OH (terramycin) and 7-Cl (aureomycin) derivatives, exist in nature, and are all well known antibiotics. Semisynthetic derivatives such as 7-dimethylamino-tetracycline (minocycline) and 6α-deoxy-5-hydroxy-tetracycline (doxycycline) are also known antibiotics. Natural tetracyclines may be modified without losing their antibiotic properties, although certain elements of the structure must be retained to do so. The modifications that may and may not be made to the basic tetracycline structure have been reviewed by Mitscher (1978). According to Mitscher, modification at positions 5–9 of the tetracycline ring system can be made without causing the complete loss of antibiotic properties.

However, changes to the basic structure of the ring system, or replacement of substituents at positions 1–4 or 10–12, generally lead to synthetic tetracyclines with substantially less, or essentially no, antibacterial activity. For example, 4-de(dimethylamino)tetracycline is commonly considered to be a non-antibacterial tetracycline.

More recently, it has been established that tetracyclines, which are rapidly absorbed and have a prolonged plasma half-life, exert biological effects independent of their antimicrobial activity (Golub et al. 1991, Golub et al. 1992, Uitto et al. 1994). Such effects include inhibition of matrix metalloproteinases (abbreviated "MMPs"), including collagenases (MMP-1; MMP-8; MMP-13) and gelatinases (MMP-2; MMP-9), as well as prevention of pathologic tissue destruction (Golub et al. 1991). Recent studies have suggested that, in some systems, certain tetracyclines and inhibitors of metalloproteinases can inhibit tumor progression (DeClerck et al. 1994) or angiogenesis (WIPO publication WO 92/12717; Maragoudakis et al. 1994). Zucker et al. (1985) showed that minocycline can inhibit melanoma cell activity in vitro. Some tetracyclines may exhibit cytotstatic effects against some tumors (Kroon et al. 1984; van den Bogert et al. 1986).

However, the use of tetracycline antibiotics, while generally effective for treating infection, can lead to undesirable side effects. For example, the long term administration of antibiotic tetracyclines can reduce or eliminate healthy microbial flora, such as intestinal flora, and can lead to the production of antibiotic resistant organisms or the overgrowth of yeast and fungi. Accordingly, chemically-modified tetracyclines, in which the antimicrobial activity is attenuated or deleted, can be preferred for use in applications in which anti-collagenolytic activity is indicated.

In view of the above considerations, it is clear that there is a need to supplement existing methods of inhibiting cancer cell invasiveness and metastasis. Current approaches rely on highly cytotoxic compounds that cause ancillary debilitating sickness in patients, or use methodology that is expensive, procedurally difficult, and unpredictable.

Accordingly, it is one of the purposes of this invention to overcome the above limitations in cancer treatment, by providing a compound and method for inhibiting the growth processes characteristic of cancer cells, including inhibiting invasiveness and metastasis, as well as inducing regression of primary tumors. In particular, it is desirable to identify new anticancer compounds and methods that inhibit cancer growth specifically and with relatively high activity, i.e., being active at doses that are substantially free of harmful side effects.

SUMMARY OF THE INVENTION

It has now been discovered that these and other objectives can be achieved by the present invention, which provides a method for inhibiting the growth or development of cancer in a mammal by providing a chemically modified tetracycline to the mammal in an amount that is effective to achieve the specified result.

In one embodiment, the invention is a method of inhibiting cancer growth in a mammal, comprising administering to the mammal a cancer-inhibitory amount of a tetracycline compound selected from the group consisting of:

4-de(dimethylamino)tetracycline (CMT-1),
  6-demethyl-6-deoxy-4-de(dimethylamino)tetracycline (CMT-3),
  4-de(dimethylamino)-7-chlorotetracycline (CMT-4), tetracycline pyrazole (CMT-5),
  6α-deoxy-5-hydroxy-4-de(dimethylamino)tetracycline (CMT-8),
  4-de(dimethylamino)-12α-deoxyanhydrotetracycline (CMT-9), and
  4-de(dimethylamino)minocycline (CMT-10).

A highly preferred tetracycline compound is 6-demethyl-6-deoxy-4-dedimethylaminotetracycline (CMT-3)

The method is useful for inhibiting growth of cancers such as carcinomas, e.g., carcinomas of the lung, prostate, breast, ovary, testes, or colon, as well as melanomas.

The method can comprise inhibiting cellular proliferation of the cancer, inhibiting invasiveness of the cancer, and/or inhibiting metastasis of the cancer.

The tetracycline compound can be administered in an amount sufficient to specifically inhibit expression of a matrix metalloproteinase by cells of the cancer or its activity in the extracellular matrix.

In a preferred aspect, the method is useful to inhibit a matrix metalloproteinase which is a gelatinase, such as gelatinase A or gelatinase B.

The method can further comprise treating the mammal with an adjunct antineoplastic modality. The adjunct antineoplastic modality can comprise chemotherapy, surgery, and/or radiotherapy.

In another embodiment, the invention is a method of inhibiting cancer growth in a mammal, comprising administering to the mammal a cancer-inhibitory amount of a tetracycline compound selected from the group consisting of:

4-de(dimethylamino)tetracycline (CMT-1), tetracyclinonitrile (CMT-2),
  6-demethyl-6-deoxy-4-de(dimethylamino)tetracycline (CMT-3),
  4-de(dimethylamino)-7-chlorotetracycline (CMT-4), and
  4-hydroxy-4-de(dimethylamino)tetracycline (CMT-6),
  4-de(dimethylamino)-12α-deoxytetracycline (CMT-7),
  6-α-deoxy-5-hydroxy-4-de(dimethylamino)tetracycline (CMT-8),
  4-de(dimethylamino)-12α-deoxyanhydrotetracycline (CMT-9), and
  4-de(dimethylamino)minocycline (CMT-10).

In another embodiment, the invention is a method of inhibiting proliferation of cancer cells, comprising contacting the cancer cells with a proliferation-inhibitory amount of a tetracycline compound selected from the group consisting of:

6-demethyl-6-deoxy-4-de(dimethylamino)tetracycline (CMT-3),
  6-α-deoxy-5-hydroxy-4-de(dimethylamino)tetracycline (CMT-8),
  4-de(dimethylamino)tetracycline (CMT-1),
  4-hydroxy-4-de(dimethylamino)tetracycline (CMT-6), and
  4-de(dimethylamino)-12α-deoxytetracycline (CMT-7).

Preferably, the tetracycline compound is
  6-demethyl-6-deoxy-4-de(dimethylamino)tetracycline (CMT-3) or
  6-α-deoxy-5-hydroxy-4-de(dimethylamino)tetracycline (CMT-8).

In another embodiment, the invention is a method of inhibiting the invasive potential of cancer cells, comprising contacting the cancer cells with an invasion-inhibitory amount of a tetracycline compound selected from the group consisting of:

6-demethyl-6-deoxy-4-de(dimethylamino)tetracycline (CMT-3),
  4-de(dimethylamino)tetracycline (CMT-1),
  4-de(dimethylamino)-12α-deoxytetracycline (CMT-7),
  4-hydroxy-4-de(dimethylamino)tetracycline (CMT-6),
  4-de(dimethylamino)-7-chlorotetracycline (CMT-4),
  6-α-deoxy-5-hydroxy-4-de(dimethylamino)tetracycline (CMT-8), and tetracyclinonitrile (CMT-2).

Preferably, the tetracycline compound is 6-demethyl-6-deoxy-4-de(dimethylamino)tetracycline (CMT-3).

In still another embodiment, the invention is a method of inhibiting the metastatic potential of cancer cells, comprising contacting the cancer cells with a metastasis-inhibitory amount of a tetracycline compound selected from the group consisting of:

4-de(dimethylamino)tetracycline (CMT-1) and
  6-demethyl-6-deoxy-4-de(dimethylamino)tetracycline (CMT-3).

In yet another embodiment, the invention is a method of treating a cancer condition characterized by excessive gelatinolytic activity, comprising administering to a mammal an amount of a tetracycline compound effective to inhibit excessive gelatinolytic activity.

In this embodiment, the cancer may be characterized by excessive activity of gelatinase A, and the tetracycline compound is selected from the group consisting of:

4-hydroxy-4-de(dimethylamino)tetracycline (CMT-6),
  4-de(dimethylamino)-12α-deoxytetracycline (CMT-7),
  6-demethyl-6-deoxy-4-de(dimethylamino)tetracycline (CMT-3),
  4-de(dimethylamino)tetracycline (CMT-1),
  6-α-deoxy-5-hydroxy-4-de(dimethylamino)tetracycline (CMT-8), 4-de(dimethylamino)-7-chlorotetracycline (CMT-4), and tetracyclinonitrile (CMT-2).

More preferably, the tetracycline compound is
4-hydroxy-4-de(dimethylamino)tetracycline (CMT-6),
4-de(dimethylamino)-12α-deoxytetracycline (CMT-7), or
6-demethyl-6-deoxy-4-de(dimethylamino)tetracycline (CMT-3).

Alternatively, in this embodiment, the cancer condition may be characterized by excessive activity of gelatinase B, and the tetracycline compound is selected from the group consisting of:
6-demethyl-6-deoxy-4-de(dimethylamino)tetracycline (CMT-3),
4-de(dimethylamino)-7-chlorotetracycline (CMT-4),
4-de(dimethylamino)tetracycline (CMT-1), and
4-hydroxy-4-de(dimethylamino)tetracycline (CMT-6).

More preferably, in this case the tetracycline compound is
6-demethyl-6-deoxy-4-de(dimethylamino)tetracycline (CMT-3) or
4-de(dimethylamino)-7-chlorotetracycline (CMT-4).

In yet another embodiment, the invention is a method of inhibiting tumor incidence in a mammal, comprising
(a) detecting in a biological sample from the mammal a gene product or metabolite associated with predisposition to a cancer prior to observing any specific cancerous lesion; and
(b) administering to the mammal a tumor incidence-inhibiting amount of a tetracycline compound selected from the group consisting of:
4-de(dimethylamino)tetracycline (CMT-1), tetracyclinonitrile (CMT-2),
6-demethyl-6-deoxy-4-de(dimethylamino)tetracycline (CMT-3),
4-de(dimethylamino)-7-chlorotetracycline (CMT-4), and
4-hydroxy-4-de(dimethylamino)tetracycline (CMT-6),
4-de(dimethylamino)-12α-deoxytetracycline (CMT-7),
6-α-deoxy-5-hydroxy-4-de(dimethylamino) tetracycline (CMT-8),
4-de(dimethylamino)-12α-deoxyanhydrotetracycline (CMT-9), and
4-de(dimethylamino)minocycline (CMT-10).

In still another embodiment, the invention is a method of inhibiting gelatinolytic activity associated with a cancerous tumor in a mammal, comprising administering to the mammal an amount of a tetracycline compound effective to inhibit gelatinolytic activity.

The gelatinolytic activity may derive from the cancerous tumor, or it may derived from normal tissue, or both. If normal tissue is involved, the normal tissue may be epithelial tissue or stromal tissue.

In yet another embodiment, the invention is a method of inhibiting cancer growth in a mammal, comprising topically administering to the mammal a cancer-inhibitory amount of a tetracycline compound selected from the group consisting of:
tetracyclinonitrile (CMT-2) and
4-hydroxy-4-dedimethylaminotetracycline (CMT-6).

In another embodiment, the invention is a method of killing cancer cells, comprising contacting cancer cells with a cytotoxic amount of a tetracycline compound selected from the group consisting of:
4-de(dimethylamino)tetracycline (CMT-1), tetracyclinonitrile (CMT-2),
6-demethyl-6-deoxy-4-de(dimethylamino)tetracycline (CMT-3),
4-de(dimethylamino)-7-chlorotetracycline (CMT-4),
4-hydroxy-4-de(dimethylamino)tetracycline (CMT-6),
4-de(dimethylamino)-12α-deoxytetracycline (CMT-7),
6-α-deoxy-5-hydroxy-4-de(dimethylamino)tetracycline (CMT-8),
4-de(dimethylamino)-12α-deoxyanhydrotetracycline (CMT-9), and
4-de(dimethylamino)minocycline (CMT-10).

In this embodiment, the cancer cells can be cells of a sarcoma or of a carcinoma, such as an adenocarcinoma. For example, the method can be used to kill cells of a carcinoma of the prostate, breast, ovary, testis, lung, colon, or breast. Preferably, the cancer cells are cells of a carcinoma of the prostate, and the tetracycline compound is 6-demethyl-6-deoxy-4-de(dimethylamino)tetracycline (CMT-3).

In yet another embodiment, the invention is a method of inhibiting the growth of a cancer in a mammal, comprising administering to a mammal having a cancer an amount of a tetracycline compound sufficient to induce differential cytotoxicity in cells of the cancer, wherein the tetracycline compound is selected from the group consisting of:
4-de(dimethylamino)tetracycline (CMT-1), tetracyclinonitrile (CMT-2),
6-demethyl-6-deoxy-4-de(dimethylamino)tetracycline (CMT-3),
4-de(dimethylamino)-7-chlorotetracycline (CMT-4),
4-hydroxy-4-de(dimethylamino)tetracycline (CMT-6),
4-de(dimethylamino)-12α-deoxytetracycline (CMT-7),
6-α-deoxy-5-hydroxy-4-de(dimethylamino)tetracycline (CMT-8),
4-de(dimethylamino)-12α-deoxyanhydrotetracycline (CMT-9), and
4-de(dimethylamino)minocycline (CMT-10).

By means of the invention, a method of killing cancer cells or inhibiting cancer growth or metastasis is provided that further avoids or mitigates side effects commonly associated with antineoplastic chemotherapeutic regimens. These and other advantages of the present invention will be appreciated from the detailed description and examples set forth hereinbelow. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the invention. The preferred embodiments of certain aspects of the invention are shown in the accompanying drawings, wherein:

FIGS. 2A to 2C are graphs illustrating the in vitro dosage-dependent inhibition of cellular proliferation by tetracycline derivatives in: LNCaP tumor cells (FIG. 2A); TSU PR1 tumor cells (FIG. 2B); and MAT LyLu tumor cells (FIG. 2C).

FIGS. 3A to 3D are graphs illustrating the in vitro dosage-dependent inhibition of cellular proliferation by tetracycline derivatives in: DU-145 tumor cells (FIG. 3A);

PC-3 tumor cells (FIG. 3B); BPH-1 non-tumorigenic prostate epithelial cells (FIG. 3C); and FHS733 normal human fibroblasts (FIG. 3D).

FIGS. 4A and 4B are graphs illustrating the in vitro dosage-dependent induction of cytotoxicity by tetracycline derivatives in Dunning MAT LyLu tumor cells (a rat prostate cancer model) at: 24 hr exposure (FIG. 4A); and 48 hr exposure (FIG. 4B).

FIG. 5A is a histogram providing a comparative illustration of the capacity of CMT compounds to inhibit invasiveness of TSU PR1 tumor cells (a human prostate cancer cell line) in vitro; FIG. 5B is a histogram providing a comparative illustration of the capacity of CMT compounds to inhibit invasiveness of MAT LyLu tumor cells in vitro.

Figure 6:
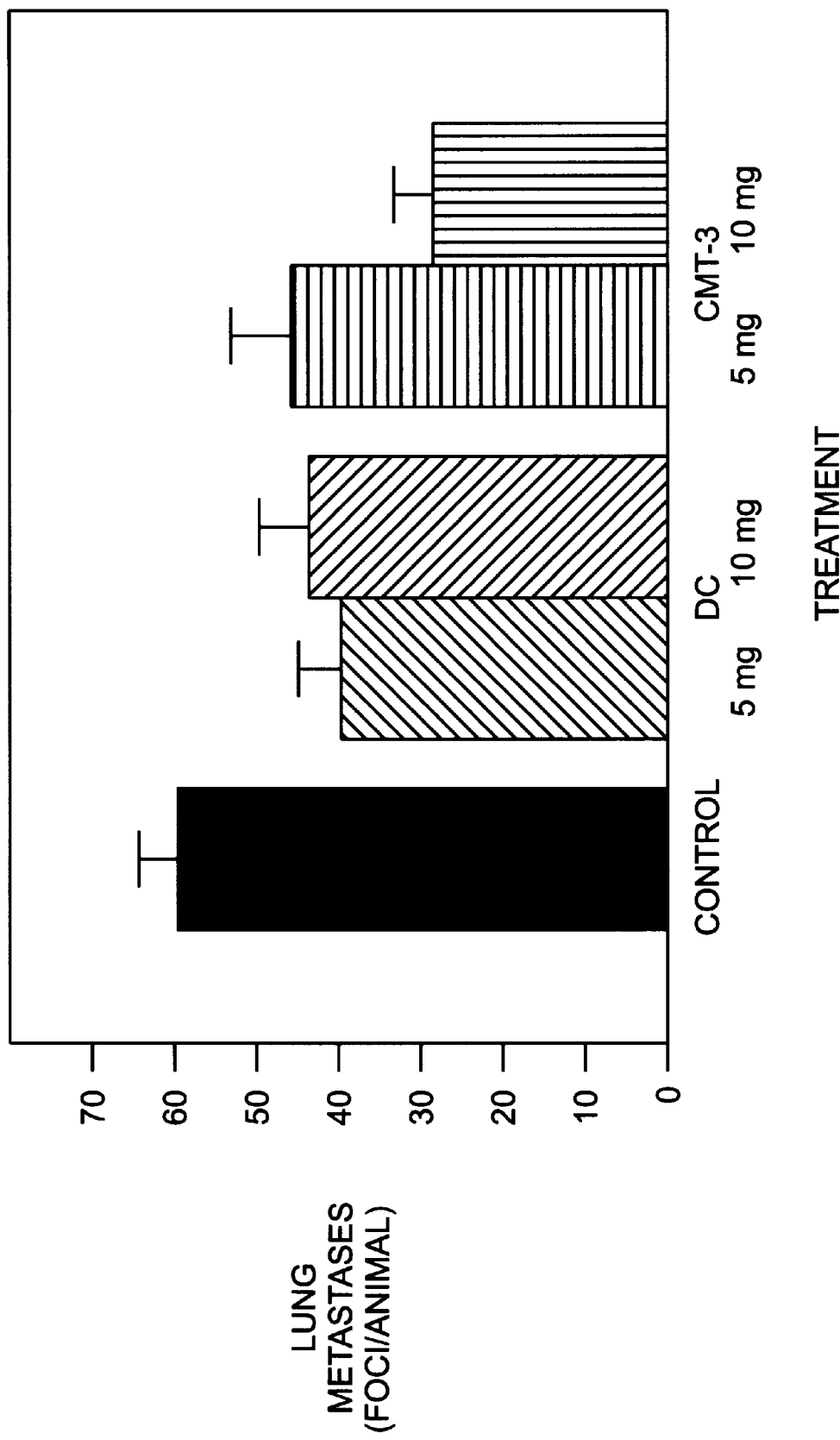

FIG. 6 is a histogram illustrating the inhibition of MAT LyLu tumor metastasis by tetracycline compounds.

FIG. 7A is a histogram demonstrating the capacity of CMT-3 to reduce tumor incidence following implantation of MAT LyLu tumor cells into test animals; FIG. 7B is a histogram illustrating the inhibition of MAT LyLu tumor metastasis by tetracycline compounds.

Figure 8:
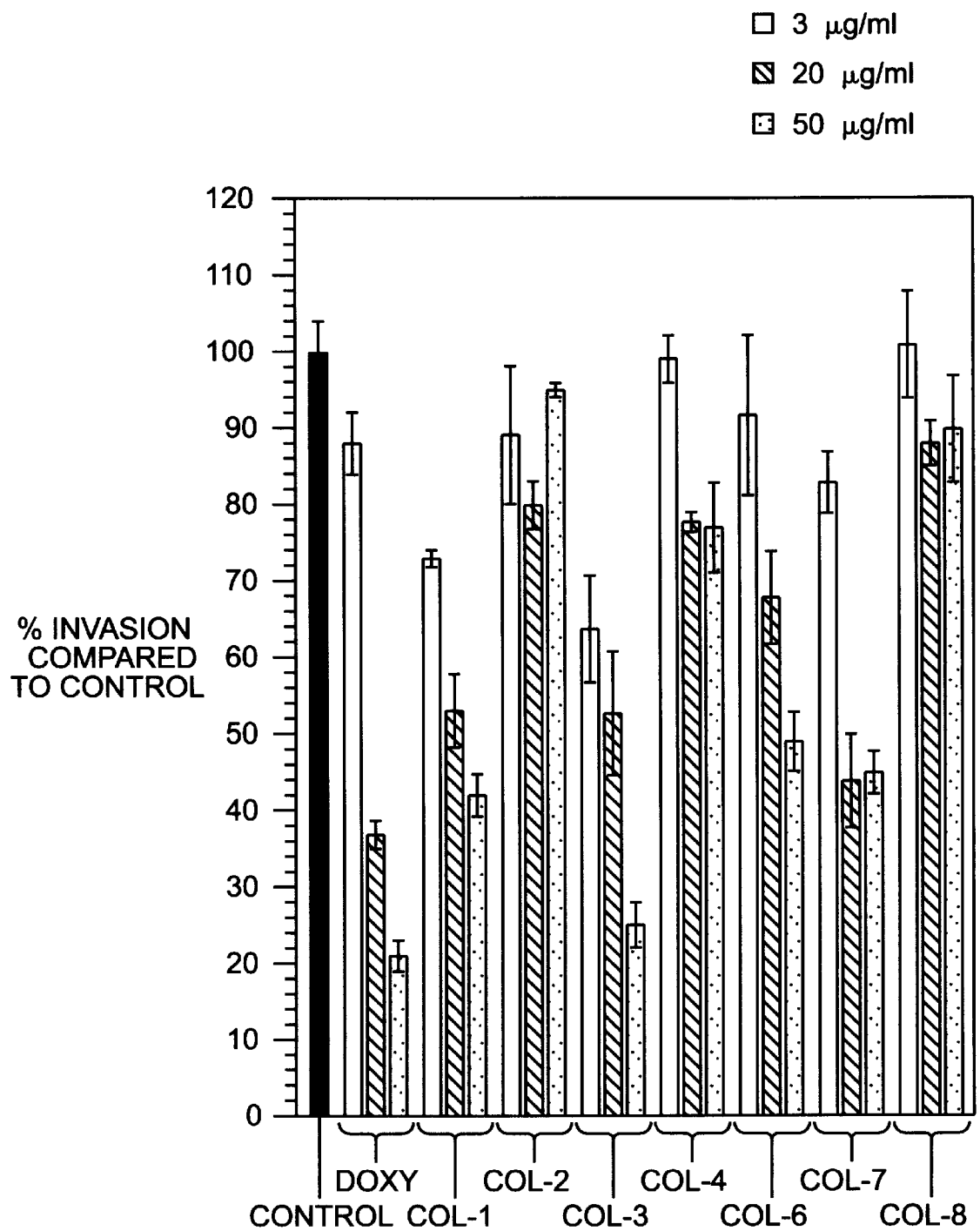

FIG. 8 is a histogram illustrating the relationship between inhibition of melanoma cell invasivity and dosage of chemically modified tetracyclines.

FIGS. 9A to 9D are graphs illustrating dosage-dependent cytotoxicity of CMT-3 in: normal prostate stromal cells (FIG. 9A); LNCaP tumor cells (FIG. 9B); PC-3 tumor cells (FIG. 9C); and DU-145 tumor cells (FIG. 9D).

FIG. 10A is a histogram showing dosage-dependent tetracycline-induced generation of nucleosomes by MAT LyLu cells; FIG. 10B shows time-dependent CMT-3-induced generation of nucleosomes by MAT LyLu cells.

DETAILED DESCRIPTION OF THE PREFERRED EMBODIMENTS

In one embodiment, the present invention is directed to a method for inhibiting cancer growth, including processes of cellular proliferation, invasiveness, and metastasis in biological systems. The method includes the use of a tetracycline compound as an inhibitor of cancer growth. Preferably, the method is employed to inhibit or reduce cancer cell proliferation, invasiveness, metastasis, or tumor incidence in living animals, such as mammals. The method is also readily adaptable for use in assay systems, e.g., assaying cancer cell growth and properties thereof.

The compounds useful according to the invention possess a desirable but unusual combination of physicochemical properties, including activity, bioavailability, solubility, and reduction of side effects. These properties render the compounds particularly desirable for the treatment of cancer.

Such compounds include, for example, those that lack the dimethylamino group at position 4 of the tetracycline ring structure, e.g., 4-de(dimethylamino)tetracycline (CMT-1),
6-demethyl-6-deoxy-4-de(dimethylamino)tetracycline (CMT-3),
7-chloro-4-de(dimethylamino)tetracycline (CMT-4),
4-hydroxy-4-de(dimethylamino)tetracycline (CMT-6),
4-de(dimethylamino)-12α-deoxytetracycline (CMT-7),
6-deoxy-5α-hydroxy-4-de(dimethylamino)tetracycline (CMT-8),
4-dedimethylamino-12α-deoxyanhydrotetracycline (CMT-9),
7-dimethylamino-6-demethyl-6-deoxy-4-de(dimethylamino)tetracycline (CMT-10),
4-de(dimethylamino)-5-oxytetracycline,
5α,6-anhydro-4-hydroxy-4-de(dimethylamino)tetracycline,
4-de(dimethylamino)-11-hydroxy-12α-deoxytetracycline,
12α-deoxy-4-deoxy-4-de(dimethylamino)tetracycline, and
12α,4α-anhydro-4-de(dimethylamino)tetracycline.

Further examples of tetracyclines modified for reduced antimicrobial activity include 6-α-benzylthiomethylenetetracycline, the mono-N-alkylated amide of tetracycline, 6-fluoro-6-demethyltetracycline, 11α-chlorotetracycline, tetracyclinonitrile (CMT-2), and tetracycline pyrazole (CMT-5).

The preferred tetracycline compounds include:
4-de(dimethylamino)tetracycline (CMT-1),
6-demethyl-6-deoxy-4-de(dimethylamino)tetracycline (CMT-3),
4-de(dimethylamino)-7-chlorotetracycline (CMT-4), and
6-α-deoxy-5-hydroxy-4-de(dimethylamino)tetracycline (CMT-8).

The most preferred tetracycline compound is 6-demethyl-6-deoxy-4-de(dimethylamino)tetracycline (CMT-3). Combinations of these compounds can be employed. Doxycycline is not included within the invention.

These compounds exhibit their cancer-inhibitory properties at concentrations that lead to fewer side effects than those of known chemotherapeutic agents, and in some cases are substantially free of side effects. For example, the useful concentrations of the compounds do not present any significant antimicrobial activity. These tetracycline compounds are useful for extended treatment protocols, where other compounds would exhibit undesirable side-effects. In addition, it is believed that the properties of hydrophilicity and hydrophobicity are well balanced in these compounds, enhancing their utility both in vitro and especially in vivo, while other compounds lacking such balance are of substantially less utility. Specifically, the compounds have an appropriate degree of solubility in aqueous media to permit absorption and bioavailability in the body, while also having a degree of solubility in lipids to permit traversal of the cell membrane to a putative site of action. The compounds are maximally effective if they can be delivered to the site of the tumor and are able to enter the tumor cells.

In the treatment of certain localized cancers, the degree of hydrophilicity of the non-antimicrobial tetracycline compound can be of lesser importance. Such compounds as tetracyclinonitrile (CMT-2) and 4-hydroxy-4-de(dimethylamino)tetracycline (CMT-6), which have low solubility in aqueous systems, can be used in direct or topical treatment of skin cancers, e.g., melanoma or basal cell carcinoma, or by implantation into the brain to topically treat brain cancer. Animal experiments, in which adult rats are orally gavaged with these two CMTs, have shown no detectable blood levels of these compounds, indicating a lack of systemic absorption and/or extraordinarily rapid excretion.

This embodiment of the invention has been developed based on the unexpected observation by Applicants that certain tetracycline compounds, chemically modified to eliminate substantially all antimicrobial activity, are effective to inhibit the proliferation, invasiveness, or metastasis of cancer cells in vitro, as well as in vivo. Of these, one especially preferred CMT, i.e., 6-demethyl-6-deoxy-4-de(dimethylamino)tetracycline (also referred to as "CMT-3"), appears to possess an excellent balance of properties, in that it is shown to possess unusually strong activity in inhibiting the cancer growth, including proliferation, invasiveness, or metastasis of cancer cells. Another advantage of CMT-3 is that it has an unexpectedly long serum half-life (approximately 28 hr). Therefore, CMT-3 may only require periodic administration, e.g., once or twice per week.

In another embodiment, the method of the invention is effective to inhibit the enzymatic activity of matrix metalloproteinases, such as collagenases and gelatinases, associated with cancerous tumors in mammals. The gelatinolytic activity capable of inhibition may derive from gelatinase expression by the cancerous tumor or from normal, i.e., non-cancerous, tissue. In particular, the gelatinase activity may be derived from such normal tissues as epithelial tissue or stromal tissue. More preferably, the method can be used to inhibit excessive gelatinolytic activity associated with such tumors. The gelatinases capable of inhibition include gelatinase A (also known as 72 kDa type gelatinase; MMP-2; type IV collagenase); and gelatinase B (also known as 92 kDa type gelatinase; MMP-9; type V collagenase). This inhibition of observed gelatinolytic activity may be due to inhibition of MMP activity, down-regulation of MMP expression, or some other interference with the physiology associated with these gelatinases, such as inhibition of activation of the precursor form of the enzyme, pro-gelatinase (or pro-MMP).

While Applicants do not wish to be bound by any particular mechanism with respect to the present invention, Applicants were surprised to find that CMTs can act, inter alia, by a fundamentally unknown mechanism in the context of cancer. Applicants have discovered that the chemically modified tetracyclines decrease the level of expression of ("down-regulate") metalloproteinases normally associated with cancer. For example, it has been found that CMT-3 reduces expression of gelatinase A by human colorectal cancer cells and inhibits expression of gelatinase B by human breast cancer cells. Applicants believe that this observation carries significant therapeutic implications for cancer treatment. Applicants also understand that these CMTs and other chemically and functionally related compounds would be useful for inhibiting the consequences of other diseases characterized by excessive gelatinase expression or activity.

The invention includes a method of inducing cytotoxicity (cell killing) in cancer cells or reducing the viability of cancer cells. The cytotoxicity of tetracycline compounds can be exploited preferably against cells of sarcomas or carcinomas, e.g., adenocarcinomas. For example, the invention can be used to induce cytotoxicity in cells of carcinomas of the prostate, breast, ovary, testis, lung, colon, or breast. The mechanism by which this cytotoxicity occurs is not completely understood, but the selective killing of the cancer cells can occur through apoptosis, necrosis, another mechanism, or a combination of mechanisms.

The killing of cancer cells can occur with less cytotoxicity to normal cells or tissues than is found with conventional cytotoxic therapeutics, preferably without substantial cytotoxicity to normal cells or tissues. For example, it has been unexpectedly observed that a tetracycline, e.g., CMT-3, can induce cytotoxicity in cancer cells while producing little or substantially no cytotoxicity in normal cells. Thus, unlike conventional cytotoxic anticancer therapeutics, which typically kill all growing cells, CMT-3 can produce differential cytotoxicity: tumor cells are selectively killed whereas normal cells are spared. Thus, in another embodiment, the invention is a method for inducing differential cytotoxicity in cancer cells relative to normal cells or tissue. This unexpected differential cytotoxicity associated with the tetracycline compounds occurs as a result of apoptosis, necrosis, another mechanism, or a combination of such mechanisms.

The data presented in the examples below, reveal that cancer cells treated with these compounds results in a decrease in extracellular gelatinolytic activity, a corresponding dose-dependent decrease in the cells' in vitro invasive potential, and a decrease in the cells' metastatic ability in vivo. Moreover, the compounds can induce killing of tumor cells, and can do so while being substantially non-cytotoxic to normal tissues. Accordingly, these chemically-modified tetracyclines can be used to suppress the formation and magnitude of metastases associated with certain cancers, used as an adjunct to other treatment regimens, and lead to greater efficacy in the treatment of metastatic cancers.

The cancers treatable by means of the present invention occur in mammals. Mammals include, for example, humans, as well as pet animals such as dogs and cats, laboratory animals such as rats and mice, and farm animals such as horses and cows.

Tumors or neoplasms include new growths of tissue in which the multiplication of cells is uncontrolled and progressive. Some such growths are benign, but others are termed "malignant," leading to death of the organism. Malignant neoplasms or "cancers" are distinguished from benign growths in that, in addition to exhibiting aggressive cellular proliferation, they invade surrounding tissues and metastasize. Moreover, malignant neoplasms are characterized in that they show a greater loss of differentiation (greater "dedifferentiation"), and of their organization relative to one another and their surrounding tissues. This property is also called "anaplasia."

Neoplasms treatable by the present invention include all solid tumors, i.e., carcinomas and sarcomas. Carcinomas include those malignant neoplasms derived from epithelial cells which tend to infiltrate (invade) the surrounding tissues and give rise to metastases. Adenocarcinomas are carcinomas derived from glandular tissue or in which the tumor cells form recognizable glandular structures. Sarcomas broadly include tumors whose cells are embedded in a fibrillar or homogeneous substance like embryonic connective tissue.

The invention is particularly illustrated herein in reference to treatment of certain types of experimentally defined cancers. In these illustrative treatments, standard state-of-the-art in vitro and in vivo models have been used. These methods can be used to identify agents that can be expected to be efficacious in in vivo treatment regimens. However, it will be understood that the method of the invention is not limited to the treatment of these tumor types, but extends to any solid tumor derived from any organ system. Cancers whose invasiveness or metastasis is associated with MMP expression, particularly gelatinase expression, are especially susceptible to being inhibited or even induced to regress by means of the invention.

Thus, the treatable cancers include, for example, colon cancer, bladder cancer, breast cancer, melanoma, ovarian carcinoma, prostatic carcinoma, or lung cancer, and a variety of other cancers as well. The invention is especially useful in the inhibition of cancer growth in adenocarcinomas, including, for example, those of the prostate, breast, kidney, ovary, testes, and colon. The invention is further useful against melanomas, which derive from the melanocytic system in the skin and other organs.

The method involves providing or administering a tetracycline compound in an amount that is effective for reducing cancer cell growth, i.e., cellular proliferation, invasiveness, metastasis, or tumor incidence in a mammal. The inhibition may result from inhibition of MMP activity, down-regulation of MMP expression, some other mechanism, or a combination of mechanisms. For example, Applicants have found that CMT-3 inhibits the expression of MMP-2 and MMP-9 in cancer cells in vitro. It is believed that all solid cancer types that express MMPs or that exhibit invasive or metastatic properties can be treated by the method of the invention. In some cases, the incidence or development of tumor foci can be inhibited or substantially prevented from occurring. Therefore, the method can be used as a prophylactic treatment, e.g., by administering the tetracycline compound to a mammal after detection of a gene product or metabolite associated with predisposition to a cancer but before any specific cancerous lesion is detected. Alternatively, the tetracycline compounds are useful for preventing cancer recurrence, for example, to treat residual cancer following surgical resection or radiation therapy. The tetracycline compounds useful according to the invention are especially advantageous as they are substantially non-toxic compared to other cancer treatments.

The effect occurs over a wide range of concentrations, including at concentrations that are extraordinarily low. The amount of the tetracycline compound used according to the invention is an amount that is effectively inhibitory of cancer growth. An amount of a tetracycline compound is effectively inhibitory to cancer growth if it significantly reduces cellular proliferation or the potential of invasiveness or metastasis. Proliferation refers to the capacity of a tumor to increase its volume through cell division, typically measured as the "doubling rate." The inhibition of cellular proliferation by the present method means that the rate of growth is decreased. In some cases, the method can actually induce regression or diminution of tumor mass, if the rate of replenishment of the tumor cells through cell division is exceeded by the rate of cell death. Invasiveness refers to the potential of a tumor or tumor cells to invade other tissues, typically by breaking down the extracellular matrix of those tissues. Metastasis refers to the potential of a tumor or tumor cells to establish new tumor foci at sites distant from the primary site where the tumor began. Typically, metastasis proceeds by individual cells or groups of cells breaking off from the primary tumor and migrating, e.g., through the blood or lymph, to establish a new tumor focus in another tissue or organ. One locus common in tumor metastasis is in the lung, where the very fine vasculature of the lung tissue can often catch circulating tumor cells, permitting the establishment of a tumor focus therein. Some types of tumors metastasize to specific types of tissues. For example, prostate adenocarcinomas can metastasize to bone with great specificity. The data presented herein provide evidence that the method of the invention is capable of inhibiting cancer growth and recurrence as defined by any or all of these parameters.

Preferably, the tetracycline compound is provided in an amount that has little or no antimicrobial activity. A tetracycline compound is not effectively antimicrobial if it does not significantly prevent the growth of microbes. Accordingly, the method can beneficially employ a tetracycline compound that has been modified chemically to reduce or eliminate its antimicrobial properties. The use of such chemically-modified tetracyclines is preferred in the present invention since they can be used at higher levels than antimicrobial tetracyclines, while avoiding certain disadvantages, such as the indiscriminate killing of beneficial microbes, and the emergence of resistant microbes, which often accompanies the use of antimicrobial or antibacterial amounts of such compounds over prolonged periods of time.

The tetracycline compounds useful according to the method of the invention appear to exhibit their beneficial effect in a dose-dependent manner. Thus, within broad limits, administration of larger quantities of a tetracycline compound has been observed to inhibit cancer cell growth or invasiveness to a greater degree than does administration of a smaller amount. Moreover, efficacy has been observed at dosages below the level at which toxicity is seen in normal cells or at the organismal level. Accordingly, one of the advantages of the invention is that the debilitating side effects usually attendant upon conventional cytotoxic cancer treatments are reduced, and preferably avoided.

The maximal dosage for a subject is the highest dosage that does not cause undesirable or intolerable side effects. For example, the tetracycline compound(s) can be administered in an amount of from about 0.1 mg/kg/day to about 30 mg/kg/day, and preferably from about 1 mg/kg/day to about 18 mg/kg/day. For the purpose of the present invention, side effects may include clinically significant antimicrobial or antibacterial activity, as well as toxic effects. For example, a dose in excess of about 50 mg/kg/day would likely produce side effects in most mammals, including humans. In any event, the practitioner is guided by skill and knowledge in the field, and the present invention includes, without limitation, dosages that are effective to achieve the described phenomena.

The invention can also be practiced by including with the tetracycline compound one or more other anti-cancer chemotherapeutic agents, such as any conventional chemotherapeutic agent. The combination of the tetracycline compound with such other agents can potentiate the chemotherapeutic protocol. Numerous chemotherapeutic protocols will present themselves in the mind of the skilled practitioner as being capable of incorporation into the method of the invention. Any chemotherapeutic agent can be used, including alkylating agents, antimetabolites, hormones and antagonists, radioisotopes, as well as natural products. For example, the non-anti-microbial tetracycline compound can be administered with antibiotics such as doxorubicin and other anthracycline analogs, nitrogen mustards such as cyclophosphamide, pyrimidine analogs such as 5-fluorouracil, cisplatin, hydroxyurea, taxol and its natural and synthetic derivatives, and the like. As another example, in the case of mixed tumors, such as adenocarcinomas of the breast and prostate, in which the tumors can include gonadotropin-dependent and gonadotropin-independent cells, the tetracycline can be administered in conjunction with leuprolide or goserelin (synthetic peptide analogs of LH-RH). Other antineoplastic protocols include the use of a tetracycline compound with another treatment modality, e.g., surgery, radiation, other chemotherapeutic agent, etc., referred to herein as "adjunct antineoplastic modalities." Thus, the method of the invention can be employed with such conventional regimens with the benefit of reducing side effects and enhancing efficacy.

The preferred pharmaceutical composition for use in the method of the invention includes a combination of the tetracycline compound in a suitable pharmaceutical carrier (vehicle) or excipient as understood by practitioners in the art.

Enteral administration is a preferred route of delivery of the tetracycline, and compositions including the tetracycline compound with appropriate diluents, carriers, and the like are readily formulated. Liquid or solid (e.g., tablets, gelatin capsules) formulations can be employed. It is among the advantages of the invention that, in many situations, the tetracycline compound can be delivered orally, as opposed to parenteral delivery (e.g., injection, infusion) which is typically required with conventional chemotherapeutic agents.

Parenteral use (e.g., intravenous, intramuscular, subcutaneous injection) is also contemplated, and formulations using conventional diluents, carriers, etc., such as are known in the art can be employed to deliver the compound.

Alternatively, delivery of the tetracycline compound can include topical application. Compositions deemed to be suited for such topical use include as gels, salves, lotions, ointments and the like. In the case of tumors having foci inside the body, e.g., brain tumors, the tetracycline compound can be delivered via a slow-release delivery vehicle, e.g., a polymeric material, surgically implanted at or near the lesion situs.

In developing the present invention, several chemically modified tetracyclines (CMTs) were tested for their effect (in comparison to a commercially available antibacterial tetracycline, doxycycline) in inhibiting cancer growth. This testing investigated the effect of these compounds on prostate cancer cell proliferation and invasive potential in vitro, and on tumor growth and lung colonization of an in vivo tumor model, the rat Dunning MAT LyLu. During in vitro experiments, antimicrobial Doxycycline and certain non-antimicrobial CMTs inhibited the cell proliferation of human prostate tumor cell lines (PC-3, DU-145, TSU PR1, and LNCaP), and the Dunning prostate tumor cells ($IC_{50}$=3–120 $\mu$g/mL). Doxycycline and CMTs also inhibited invasive potential by 10% to 90%, depending on the compound. CMT-3 (6-deoxy-6-demethyl-4-de(dimethylamino) tetracycline) was the most potent of the tetracycline analogues, inhibiting invasive potential by 90% at 5 $\mu$g/mL, a level of this drug readily achieved in vivo by oral administration. Growth of the Dunning tumor at the primary site (s.c.) was not altered significantly in rats treated with either doxycycline or CMT-3 by oral gavage daily for 21 days following tumor implant. There was a significant decrease, however, in the number of lung metastases: 28.9±15.4 sites/animal in the CMT-3-treated group versus 59.5±13.9 sites/animal in controls (p<0.01), which is double the effect seen with doxycycline at the same oral dose. Predosing the rats 7 days prior to tumor implant resulted in a significant delay in tumor growth (46±9.3%, p<0.05) and a reduction in metastasis. In addition, tumor remission (inhibition of tumor incidence) occurred in the groups treated with CMT-3 (40 mg/kg). Treatment with doxycycline, however, did not result in tumor remission. In addition, a 58±8% decrease in the number of lung metastases was observed in the CMT-3-treated group versus a decrease of 33±7.0% in the doxycycline group. No significant drug-induced morbidity was observed in any of the experiments described herein. These results further substantiate the usefulness of CMT-3 for chemotherapeutic treatment to control tumor aggression and prevent metastasis.

In other experiments described hereinbelow, we examined the effect(s) of doxycycline and CMTs on extracellular levels of gelatinase A and B activity from a highly invasive and metastatic human melanoma cell line C8161, and correlated these observations with changes in the cells' biological behavior in an in vitro invasion assay and in an in vivo SCID mouse model. The results indicate that coincident with the ability of these compounds to differentially suppress extracellular levels of gelatinase activity, C8161 cells treated with doxycycline and CMT-1, CMT-3, and CMT-6 were less invasive in vitro, in a dose dependent manner (3–50 $\mu$g/mL). Furthermore, data derived from the in vivo model indicate that SCID mice dosed orally with CMT-1 and CMT-3 contained a reduced number of lung metastases following intravenous injection of C8161 cells via tail vein inoculation.

The following examples are provided to assist in a further understanding of the invention. The particular materials and conditions employed are intended to be further illustrative of the invention and are not limiting upon the reasonable scope thereof.

EXAMPLE 1A

Inhibition of Enzyme Expression in Cancer Cells

Two human cancer-derived cell lines were obtained from the American Type Culture Collection (ATCC) in Rockville, Md. The cell lines included COLO 205, a human colon cancer-derived cell line that expresses MMP-2 or gelatinase A, and E-10, a human breast cancer-derived cell line that expresses MMP-9 or gelatinase B.

Cells of each cell line were cultured in 75 $cm^2$ T-flasks in RPMI-1640 (Gibco) with 10% heat-inactivated fetal bovine serum (FBS) containing 100 units/mL penicillin and 100 $\mu$g/mL streptomycin. The cells were fed every two days, and passaged every week. The cells were grown to 80–90% confluence, and then the FBS-containing medium was replaced with a serum-free medium (SFM). CMT-3 (CollaGenex Pharmaceuticals, Inc., Newtown, Pa.) was added in several concentrations to the cells in SFM. Conditioned medium was collected after 24 hr, centrifuged to remove cell debris, and then assayed for MMP protein expression by Western blot using a conventional technique, and scanning the blots with a laser densitometer. The data obtained are summarized in Table 1, below.

TABLE 1

Percent Inhibition of MMP Protein Expression in Cancer Cell Lines by CMT-3

| Cancer Cell Line | CMT-3 Concentration | | |
|---|---|---|---|
| | 0 $\mu$M | 10 $\mu$M | 20 $\mu$M |
| COLO 205 (expressing MMP-2) | — | 13.3% | 66.9% |
| E-10 (expressing MMP-9) | — | 45.3% | 60.8% |

These data clearly show dose-dependent activity of CMT-3 in inhibiting expression of two different MMPs in two different types of cancer cells. It is believed that the inhibition of MMP expression inhibits the ability of these cancer cells to degrade the extracellular matrix of healthy tissues thereby limiting the cancer's ability to invade such healthy tissues. The inhibition of cancer cell proliferation in vitro and cancer metastasis in vivo is demonstrated in several following examples.

EXAMPLE 1B

Inhibition of Matrix Metalloproteinase Activity in Cancer Cells

The effects of CMT-3 and doxycycline on gelatinase activity or expression by prostate cancer cells were tested. First, we tested the capacity of CMT-3 and doxycycline to inhibit MMP secretion into culture medium. Gelatinase activity was measured using a method adapted from the method of Dean and Woessner (1985). Conditioned culture medium was collected from MAT LyLu and TSU PR1 cells treated with CMT-3 or doxycycline for two days. The serum-free culture medium comprised RPMI 1640 basal medium containing insulin (5 $\mu$g/mL), transferrin (5 $\mu$g/mL), selenious acid (5 ng/mL), and gentamicin (2 $\mu$g/mL). Initial assays of these conditioned media showed the presence of TIMPs which interfered with the MMP assay. Therefore the conditioned media were chemically reduced (1 mM dithiothreitol) and alkylated (1 mM iodoacetamide) each for 30 min at 37° C., and then dialyzed to destroy endogenous TIMPs. (Dean et al. 1987; Woessner 1991.) The dialyzed medium was assayed for gelatinase activity following activation of latent MMPs with 1 mM p-aminophenyl mercuric acetate (APMA) for 30 min at 37° C. The assay mix was 25 $\mu$g $^3$H-gelatin (prepared from heat-denatured $^3$H-acetylated acid-soluble collagen), 0.1 mL of processed culture-conditioned medium, 1 mM phenylmethyl sulfonyl fluoride (PMSF) in a total volume of 0.5 mL of an assay buffer (20 mM Tris-HCl, pH 7.4, 30 mM NaCl, 0.005% Brij35, 10 mM $CaCl_2$, 2 µM $ZnSO_4$, and 0.02% $NaN_3$). In some cases, 1 mM $CaCl_2$ (instead of 10 mM) was used. Blanks were obtained by adding 1 mM 1,10-phenanthroline. Doxycycline or CMT-3 were added to the assay mixture following activation of the latent MMPs and just before adding the substrate $^3$H-gelatin.

In addition, the ability of doxycycline or CMT-3 to inhibit APMA activation of MMPs was tested. Processed culture-conditioned medium was incubated with the drugs for 1 hr before adding 1 mM APMA, and the incubation was continued thereafter for 2 hr. $^3$H-gelatin was then added and the assy was continued for 4 hr. All assays were performed in duplicate tubes, and repeated at least twice.

MMP activity in the culture media was examined at 1 mM and 10 mM $CaCl_2$, with no change in $[Zn^{2+}]$ in the assay buffer. We employed 1 mM $CaCl_2$, as this concentration is closer to physiological concentration, and 10 mM $CaCl_2$, as it is reported to be the optimum concentration in in vitro assays (Woessner 1991). As is shown in Table 2, both CMT-3 and doxycycline inhibited in vitro activated gelatinases. At 1 mM $CaCl_2$, the 50% inhibition dose ($IC_{50}$) of CMT-3 was 0.5 µM, while at 10 mM $CaCl_2$, the $IC_{50}$ for CMT-3 was ~1.5 µM. By contrast, at 10 mM $CaCl_2$, the $IC_{50}$ for doxycycline was 5.0 µM. Furthermore, both of these drugs strongly inhibited activation of MMPs by p-aminophenyl mercuric acetate; the $IC_{50}$ for CMT-3 was 1.0 µg/mL (2.2 µM), and for doxycycline was 2.5 µg/mL (5 µM) at 10 mM $CaCl_2$.

TABLE 2

Enzyme Inhibition by CMT-3 and Doxycycline in Prostate Cancer Cells

| | Percent Inhibition | | | |
|---|---|---|---|---|
| Drug | CMT-3 | | Doxycycline | |
| Concentration (µM) | 1 mM $CaCl_2$ | 10 mM $CaCl_2$ | 1 mM $CaCl_2$ | 10 mM $CaCl_2$ |
| 0.25 | ND | 31.5 ± 1.2 | ND | ND |
| 0.50 | 84.8 ± 10.1 | 37.8 ± 7.5[b] | 54.8 ± 0.6[a] | ND |
| 1.0 | 96.7 ± 4.6[a] | 45.1 ± 2.9 | 77.4 | 0.0 |
| 2.0 | ND | 51.2 ± 2.6 | ND | ND |
| 5.0 | 97.2 ± 2.9 | 52.4 ± 3.5 | ND | 64.3 ± 19.5 |
| 10 | 100 | 69.9 ± 10.5 | 91.2 ± 3.3 | 75.5 ± 3.3 |
| 20 | ND | 78.9 ± 11.4 | ND | 85.1 ± 3.5 |
| 50 | ND | 94.2 ± 3.3 | 100 | 93.2 ± 2.7 |
| 100 | ND | ND | ND | 91.2 ± 2.6 |

[a]Total gelatinase activity in the presence of 1 mM $CaCl_2$, without inhibitors (control) was 18.95 ± 3.18 ng [$^3$H]gelatin digested/min/mL of the dialyzed medium.
[b]Total gelatinase activity in the presence of 10 mM $CaCl_2$, without inhibitors (control) was 48.92 ± 2.7 ng/min/mL.

Next we examined whether CMT-3 and doxycycline differentially affect the production of two major classes of gelatinases: gelatinase A (MMP-2) and gelatinase B (MMP-9). Confluent cultures of TSU PR1 and MAT LyLu cells were incubated with various concentrations of doxycycline and CMT-3 for 48 hours in serum-free medium. The conditioned media were then analyzed for MMPs by zymography as described below.

Conditioned media were collected from the cultures that had been treated with doxycycline or CMT-3 for 2 days. Media were then incubated with SDS-gel electrophoresis sample buffer for 30 min at room temperature, and then analyzed by gel electrophoresis on SDS-polyacrylamide gel (8%) containing gelatin (1 mg/mL). Following electrophoresis, the gels were washed twice with 0.25% TRITON® X100 for 30 min each, and incubated for 18 hr at 37° C. in an MMP digestion buffer comprising 20 mM Tris-HCl, pH 7.4, containing 30 mM NaCl, 1 mM PMSF, 10 mM $CaCl_2$, 2 µM $ZnSO_4$, 0.005% Brij35, and 0.02 $NaN_3$ (Lokeshwar 1993a). After incubation, the gels were briefly rinsed in distilled water and stained with 0.25% Coomassie brilliant blue R250 prepared in 40% isopropanol solution for 1 hr. Gels were destained with 7% acetic acid, the locations of MMPs in the gels were visible as clear areas on a blue background, indicative of digested gelatin.

Figure 1A:
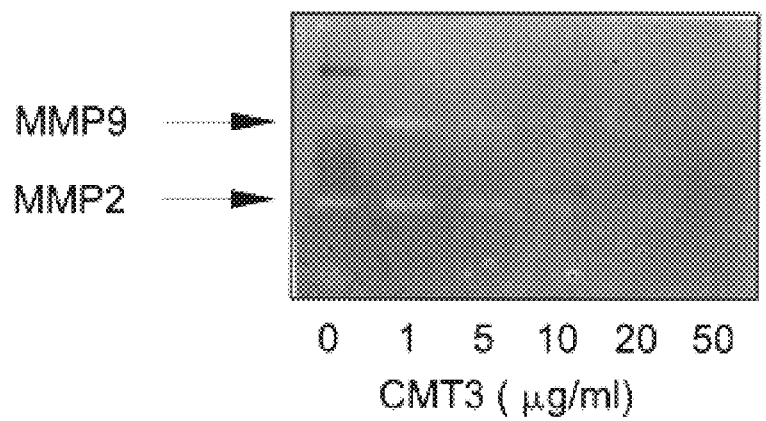
FIGS. 1A to 1D are four electrophoretograms depicting zymographic analysis of conditioned media obtained from prostate cancer cells in vitro illustrating the effects of CMT-3 and doxycycline on MMP activity: TSU PR1 prostate tumor cells treated with CMT-3 (FIG. 1A) or doxycycline (FIG. 1B); MAT LyLu prostate tumor cells treated with CMT-3 (FIG. 1C) or doxycycline (FIG. 1D).
Figure 1B:
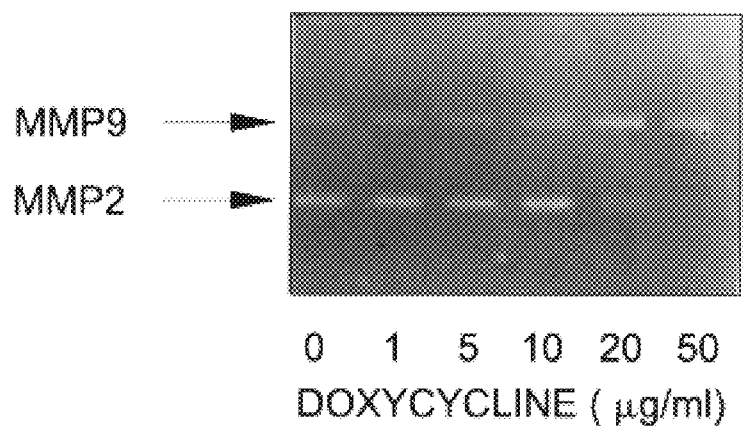
Figure 1C:
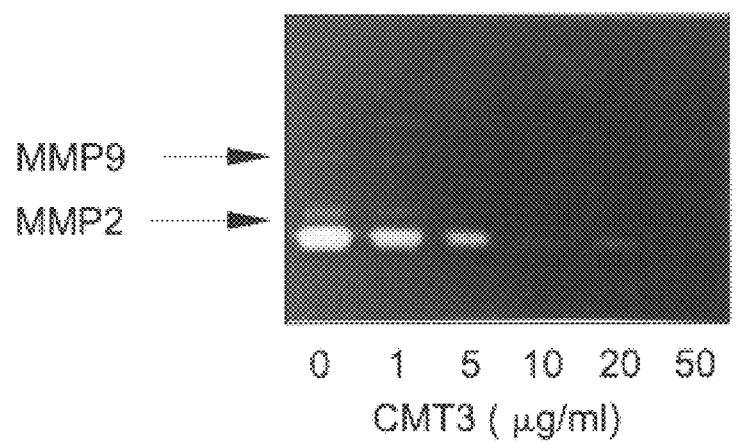
Figure 1D:
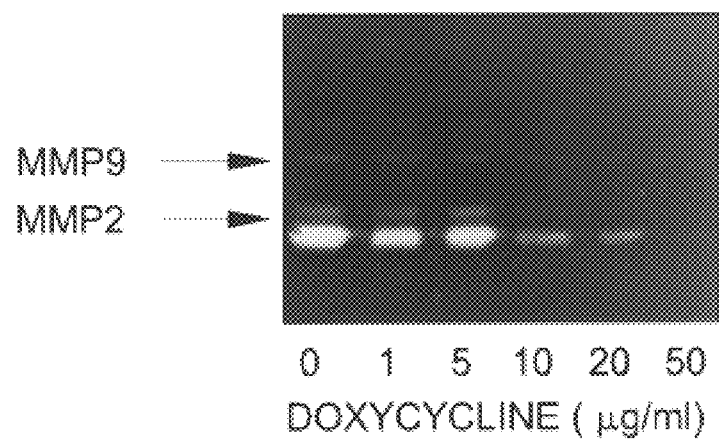

The results are shown in FIGS. 1A to 1D. The conditioned media derived from both cell lines contained predominantly MMP-2 and MMP-9. The TSU PR1 medium contained predominantly the latent forms of these two enzymes (FIGS. 1A and 1B), whereas the MAT LyLu medium contained activated MMP-2 but little MMP-9 (FIGS. 1C and 1D).

Both drugs produced a dose-dependent decrease in MMP-2 levels. CMT-3, however, decreased MMP-2 and MMP-9 levels at a lower concentration than did doxycycline. Moreover, MMP-9 levels did not decrease significantly with an increase in doxycycline concentration. The decrease in MMP levels with increasing concentration of the two tetracycline compounds was specific to MMPs, because all lanes were loaded with the same total amount of protein.

EXAMPLES 2–6

In Examples 2–6, below, the following materials and methods were employed:

Reagents: Chemically modified tetracyclines were prepared according to known methods. The synthesis of various CMTs is extensively documented. See, e.g., Mitscher (1978). The following CMTs were investigated: 4-de(dimethylamino)tetracycline (CMT-1), tetracyclinonitrile (CMT-2), 6-demethyl-6-deoxy-4-de(dimethylamino)tetracycline (CMT-3), 4-de(dimethylamino)-7-chlorotetracycline (CMT-4), 4-hydroxy-4-de(dimethylarnino)tetracycline (CMT-6), 4-de(dimethylamino)-12α-deoxytetracycline (CMT-7), and 6-α-deoxy-5-hydroxy-4-de(dimethylamino)tetracycline (CMT-8). Highly purified CMT-3 (93–98%) used for animal studies was supplied by CollaGenex, Inc., Newtown, Pa. Doxycycline was purchased from Sigma Chemical Co., St. Louis, Mo. Matrigel, a solubilized preparation of tumor basement membrane, was obtained from Collaborative Research, Bedford, Mass. Boyden Chemotaxis assay chambers (Transwells) were obtained from Costar/Corning Corp., Boston, Mass. All other reagents were from Sigma Chemical Co.

Cells and Tumor Lines: Human prostate cancer cell lines: PC-3, DU-145, and LNCaP were obtained from American Type Culture Collection, Rockville, Md. TSU PR1 and ALVA 101, human metastatic prostatic cancer cell lines, and BPH-1, a non-tumorigenic prostate cell line were also used (Lokeshwar 1995b, 1996; Hayward (1995). Cultures were maintained in complete medium composed of RPMI-1640 medium with 10% fetal bovine serum and 10 µg/mL gentamicin. The Dunning MAT LyLu rat tumor line is an androgen-insensitive prostate tumor model that metastasizes to lymph node and lungs in Copenhagen rats. MAT LyLu cells were maintained in the complete medium with added 250 nM dexamethasone.

Tumor Generation and Treatment: Dunning MAT LyLu cells were harvested from culture flasks, and a 0.5 mL suspension containing from $2 \times 10^5$ to $2 \times 10^6$ cells/mL was inoculated into the dorsal flank of adult Copenhagen rats (Harlan Sprague Dawley, Indianapolis, Ind.). The rats weighed 250–300 g, and were 90–100 days old. Tumors were detected by palpating the skin around the site of injection starting 3 days following implant of the tumor cells (Lokeshwar et al. 1995a).

Drug Treatment In Vivo: Doxycycline and CMT-3 were dissolved in a 2% aqueous solution of a soluble form of carboxymethyl cellulose (Sigma Cat. No. C-5678), and a fresh solution was made up daily. Rats were gavaged daily with 1 mL of the drug solution (concentrations specified below), or the vehicle (2% carboxymethyl cellulose). Tumor growth was recorded three times a week, and rats were weighed weekly. The effect of various treatments on tumor growth was monitored over time using calipers, and the volume approximated to an ellipsoid (i.e., volume=length× width×height×0.5236) (Lokeshwar et al. 1993b). Tumor growth rate was determined by regression analysis of tumor volume versus time, for each tumor-bearing rat. Mean tumor growth rate (time to reach a fixed volume) for each treatment group was then used to evaluate the statistical significance of treatment efficacy using the INSTAT statistical program (Ravitz Software, San Diego, Calif.). Rats were euthanized once the tumor volume reached $\geq 10$ cm$^3$. At that time animals were necropsied, tumors and lungs were removed and fixed in Bouin's fixative. Macroscopic tumor foci on the lungs were counted under a dissecting microscope.

EXAMPLE 2
Effect of CMTs on Prostate Cancer Cell Proliferation In Vitro

To determine the cytotoxicity of CMTs on prostate tumor cell lines, TSU-PR1 cells (and cells of other tumor cell lines) were exposed to various CMTs or to doxycycline for 24 hr or 48 hr in a complete medium. Cell viability (percent of live cells) was estimated by counting the cells following trypan blue staining. Cellular viability was also estimated by the tetrazolium dye reduction assay (MTT assay) (Lokeshwar et al. 1995b). Due to the aggressive proliferative capacity of cancer cells, it is assumed that viable cells are actively proliferating. Therefore, the measurement of viability was used as an estimate of proliferation. Results are expressed as Mean±SEM from three separate experiments.

It was found that doxycycline and several CMTs reduced cellular viability and, hence, inhibited cell proliferation, in vitro. Inhibition of cell proliferation was proportional to the concentration of the drugs and duration of exposure, but varied considerably from compound to compound. In particular, CMT-2 and CMT-3 were significantly more cytotoxic than doxycycline. For the two human prostate cancer cell lines DU-145 and TSU-PR1, the 50% inhibition dose (IC$_{50}$) for various CMTs ranged from 2.7 µg/mL (CMT-3, 48 hr exposure) to 120 µg/mL (CMT-6). The IC$_{50}$ for CMT-2 was 5.7 µg/mL. CMT-5 was not inhibitory. Representative results are illustrated for the cell lines LNCaP, TSU PR1 and MAT LyLu in which a panel of CMTs was tested along with doxycycline (FIGS. 2A–2C); and for the cell lines DU-145, PC-3, BPH-1 and FHS733 (a normal human fibroblast cell line) against which (FIGS. 3A–3D).

EXAMPLE 3A
Cytotoxic Effect of CMTs on MAT LyLu Cells In Vitro

Similar results were obtained when doxycycline and several CMTs (CMT-2, CMT-3, and CMT-6) were tested on the Dunning MAT LyLu cells in vitro. The Dunning MAT LyLu cells were exposed to the drugs for 24 hr or 48 hr before estimating the cellular viability. Cell viability was estimated by trypan blue staining following exposure to the drugs. The results of these studies are summarized in FIG. 4A (24 hours) and FIG. 4B (48 hr). Data are presented as Mean±SEM from three separate experiments. CMT-3 and CMT-2 were the most effective inhibitors of cell proliferation in this assay.

EXAMPLE 3B
Effect of CMT-3 on Prostate Cancer Cell Proliferation In Vitro

Based on the data described above, it appeared that CMT-3 was the most potent (most cytotoxic) of all of the tested CMTs in vitro. To confirm this observation, we compared the cytotoxicities of CMT-3 and doxycycline for a panel of common human prostate cancer cell lines. Cytotoxicity was measured using the MTT assay (see above) and a cellular thymidine incorporation assay as described by Lokeshwar et al. (1995a). The 50% growth inhibition (GI$_{50}$) values obtained using both assays were identical. As shown in the data summarized in Table 3, below, CMT-3 was two- to eight-fold more cytotoxic than doxycycline.

TABLE 3

Cytotoxicity of CMT-3 and Doxycycline Against Prostate Cancer Cell Lines

| Cancer Cell Line | Cytotoxicity GI$_{50}$ (µM) | |
|---|---|---|
| (Number of Replicate Experiments) | Doxycycline | CMT-3 |
| ALVA 101 (4) | 36.6 ± 2.42 | 6.82 ± 0.75 |
| BPH-1 (3) | 21.3 ± 5.4 | 10.53 ± 3.7 |
| DU 145 (8) | 43.6 ± 9.36 | 5.06 ± 1.18 |
| LNCaP (5) | 13.86 ± 2.97 | 5.0 ± 2.1 |
| MAT LyLu (7) | 20.0 ± 6.4 | 5.2 ± 1.9 |
| PC-3 (5) | 36.4 ± 2.5 | 10.56 ± 2.1 |
| TSU PR-1 (5) | 41.0 ± 11 | 14.74 ± 2.64 |

Growth inhibition was calculated from linear regression of the dose-response curves generated for each experiment using log(dose) vs. cell proliferation (% of control). Correlation coefficient (r) was always >0.95 (negative). Results are presented as Mean±SEM of at least three GI$_{50}$ values calculated from each experiment.

EXAMPLE 4
Effect of CMTs on Invasive/Metastatic Potential of Prostate Cancer Cells Treating prostate cancer cells with certain CMTs significantly inhibited the cells' ability to invade an artificial construct of tumor basement membrane (Lokeshwar et al. 1996). In this method, 4×10$^5$ tumor cells were plated on the top chamber of the Boyden chemotaxis assay chambers (Costar Transwell plates). The bottom side of the chamber was a 12 µm-pore polycarbonate filter layered with 0.5 mm thick layer of Matrigel. The bottom well contained a chemoattractant, a serum-free culture-conditioned medium from FHS 733 cells, a line of human fetal lung fibroblasts (ATCC No. HTB-157). Cancer cells (4×10$^5$) were plated in the top wells of the plates. Doxycycline or CMTs were diluted in a serum-free medium to 5 µg/mL, and were added to both top and bottom chambers. The control wells contained only 0.1% dimethyl sulfoxide (DMSO, a diluent). After 48 hr incubation, MTT was added to both the top and bottom wells (0.5 mg/mL), and incubation was continued for 4 hr. Wells were then emptied, and the cells from the undersides of the filter were pooled with those in the bottom wells with a filter tip. The reduced MTT (formazan) from top and bottom wells was solubilized with DMSO overnight, and absorbance (O.D.) at 515 nm was measured. The ratio of the O.D. from the bottom wells to that of the total (i.e., O.D. of top plus bottom wells) was taken as the invasive potential. This procedure was consistently superior to that used in earlier reports (Albini et al. 1987), where cells on the bottom sides of the filters were counted from several randomly chosen optical fields. The MTT assay procedure also normalizes the coincident inhibition due to the cytotoxic effects of the agents under investigation. Results presented are from three independent experiments.

The effect of CMT-3 and other tetracycline compounds on the invasive potential of TSU-PR1 and the Dunning MAT LyLu cells was evaluated using the Matrigel assay. As shown in FIG. 5A, the ability of these compounds to inhibit invasive activity varied significantly. CMT-3 was the most potent, and CMT-7 the least potent, inhibitor of the invasive/metastatic potential of TSU-PR1 cells. The CMTs were surprisingly effective in comparison to a common tetracycline, doxycycline, which caused only a modest (8±1.8%) inhibition of Matrigel invasion of TSU-PR1 cells.

In particular, the 50% inhibitory dose ($IC_{50}$) calculated for various CMTs varied from 1.7±0.31 μg/mL for CMT-3 to >100 μg/mL for CMT-7. Doxycycline was not significantly inhibitory in TSU PR1 cells, ($IC_{50}$=27±4.3 μg/mL). The $IC_{50}$ values for CMT-3 and doxycycline with respect to three other invasive human prostate cancer cell lines (DU 145, PC-3, and ALVA 101) were in the same concentration ranges as for TSU PR1 (data not shown).

In the Dunning cells, both CMT-2 and CMT-3 equally inhibited Matrigel invasion. See FIG. 5B. Moreover, doxycycline also significantly inhibited (68±4.2%) the invasive/metastatic potential of the Dunning MAT LyLu cells over a 48 hr period. Continuous presence of the drugs was needed to achieve significant inhibition of invasive potential. Forty-eight hour pretreatment with CMT-3, followed by deletion of the drugs in the invasion chamber, had only a moderate effect on the invasive potential.

The 48 hr invasion assay had the following invasion indices in the control wells (0.1% DMSO): 22±8.3 for TSU-PR1 cells and 17±4.2% for MAT LyLu cells.

EXAMPLE 5

Effect of CMT-3 on MAT LyLu Tumor Growth and Lung Metastasis

CMT-3 and doxycycline were tested for antitumor activity in vivo. In this series of experiments, daily gavage of drugs was started on the same day on which tumor cells were implanted in the test animals. Tumor growth was initiated by sub cutis injection of $1 \times 10^6$ tumor cells.

Tumors were palpable (>0.1 $cm^3$) in more than 50% of injected animals by day 6, and in 100% of the animals by day 12. Tumors rapidly increased in volume, reaching >10 $cm^3$ by 15 days post-implant. Tumor growth rate, as determined by the time to reach a volume of 3 $cm^3$, did not vary significantly between rats treated with doxycycline or CMT-3 at concentrations of 20 mg/kg or 40 mg/kg, and rats given the vehicle alone (2% solution of carboxymethyl cellulose). Regression analysis of tumor volumes showed no significant difference in the primary tumor growth between the control group and the doxycycline- and the CMT-3-treated groups. Specifically, the time period from injection of cells to a growth of 3 $cm^3$ tumor was 13.57±2.12 days in the control group and 14.0±1.9 days in the CMT-3-treated group. All of the tumors, from the control group as well from the drug-treated group developed highly necrotic centers as the tumors grew to 10 $cm^3$ or larger.

Metastatic tumor foci (MTF) were visible in lungs fixed in Bouin's fixative. Most of the MTF were less than 1 mm in diameter in all the treatment groups. FIG. 6 shows the number of metastatic foci in the lungs (Mean±SEM). As illustrated in FIG. 6, the control group showed 59.5±13.9 MTF/rat (Mean±SD) and only 39.7±17.2 or 43.6±18.8 MTF/rat in low dose (20 mg/kg) and high dose (40 mg/kg) doxycycline-treated group, respectively. The high-dose CMT-3 group (10 mg/rat, i.e., 40 mg/kg) had the most significant reduction in MTF, 28.9±15.4 MTF/rat, a 51% reduction in MTF relative to the control group (p<0.01, Tukey Kramer Multiple comparison test). Histological examination of the lung sections did not reveal any apparent differences in tumor foci among various treatment groups.

EXAMPLE 6

Effect of Pretreatment on Tumor Growth and Metastasis

In another series of experiments, we examined whether predosing host animals with the drugs would affect tumor growth and metastasis. Daily gavage of control or drugs (doxycycline or CMT-3; 40 mg/kg) was begun 7 days prior to the injections of the MAT LyLu tumor cells ($2 \times 10^5$ cells/animal) and continued for a total of 21 days.

Using this schedule, we found a decrease in tumor incidence and tumor growth rate. Tumor growth rates were calculated from thrice-weekly measurement of tumor volume with linear regression analysis of log-transformed volume measurements (Dudak et al. 1996). Tumor growth rates determined by this method were then tested by Tukey-Kramer multiple comparison test and were found to be significantly different from the control group.

As shown in FIG. 7A, tumor incidence was >90% in the control and doxycycline-treated groups in three independent experiments. Surprisingly, however, tumor incidence in CMT-3-treated rats varied from 28% (2/7) to 85% (6/7) in four separate experiments. Thus, tumor incidence was significantly lower (by 55%±18) than for the control or doxycycline-treated groups. The rats with no primary tumor incidence remained tumor-free for up to six months, at which time they were euthanized. No histologically identifiable tumor foci were observed, whether at the site of injection or in the lungs. Furthermore, a preparation of CMT-3 of greater purity reduced the tumor incidence to 43% (data not shown). Thus, only CMT-3, and not the commercially available tetracycline, doxycycline, produced significant inhibition of primary tumor incidence.

In addition, among the rats in the CMT-3-treated group that developed measurable tumors ($\leq 50\%$), the tumor growth rate (time to reach tumor volume of 3 $cm^3$) was significantly slower (20.2±3.5 days) than in either the control group (15.9±2.0) or the doxycycline-treated group (16.7±1.9 days). It should be emphasized that the tumor growth rate was calculated from the subset of animals in which the tumors were measurable. Thus, the overall effect of CMT-3 on tumor growth was greater than that suggested by these data.

Applicants were especially surprised by the apparent remission of palpable tumors (i.e., tumor resorption; reduction of tumor size) in rats treated with CMT-3 (30%) or doxycycline (20%) in two separate experiments. In those animals, tumors were palpable by 8–10 days after injection at the primary site, but the tumors did not increase in volume, and disappeared 4–7 days later. These rats with no primary tumor incidence remained tumor-free and healthy up to eight months, at which time they were euthanized.

CMT-3 also inhibited tumor metastasis by predosing the animals with CMT-3. See FIG. 7B. This effect was comparable to that observed without predosing. The MTF in treated animals was 46.3±6.7 in the CMT-3-treated group versus 74.2±6.4 in controls, a 37.5% decrease. Data presented are expressed as Mean±SD from all the animals in which tumors grew to a size of $\geq 10$ $cm^3$. The lungs removed from tumor-free animals were free of histologically recognizable metastasis.

None of the typical adverse effects of conventional chemotherapeutic drug treatments, such as irritability, hypersensitivity to light, hair loss, or diarrhea were observed in association with the tetracycline treatments described hereinabove. As a gross measure of injury to normal tissue plausibly caused by doxycycline or CMT-3, animals were weighed before, during, and after treatment, and all changes were examined. In all experiments, none of the animals showed a significant weight loss, instead, there was a 3% (control group) to 12% (CMT-3 treated group) gain in body weights as of the time the experiment was terminated (6-month post-treatment observation period). Thus, the method of the invention has a substantial advantage over such conventional anti-cancer therapies inasmuch as less, and preferably virtually no, toxicity to normal tissue is seen at cancer-inhibitory tetracycline dosages.

EXAMPLES 7–10

In Examples 7–10 below, the following materials and methods were employed:

Cell Culture and Maintenance: C8161 cells, a human melanoma cell line, were maintained in Dulbecco's modified Eagle's medium (DMEM, GIBCO, Grand Island, N.Y.), supplemented with 10% heat-inactivated fetal bovine serum (FBS; GIBCO) and 0.1% gentamicin sulfate. These cells were routinely screened for Mycoplasma contamination using the GenProbe Rapid Detection System (Fisher Scientific; Chicago, Ill.).

Chemically Modified Tetracyclines: Fresh stock solutions of the chemically modified tetracycline compounds (2 mg/mL) were prepared for each experiment by hydrating in 2% dimethyl sulfoxide (DMSO)/water pH 10, then adjusting to pH 7.4 using 1.0 M HCl.

EXAMPLE 7

Effect of Chemically Modified Tetracyclines on Cell Proliferation

One hundred thousand ($1 \times 10^5$) C8161 cells were seeded per well in each of three 24-well culture dishes in the presence of either DMSO (0.05%; Sigma Chem. Co.; control) or 50 µg/mL of doxycycline or the other CMTs (three wells on each plate per compound). Cells were harvested from the first plate after 24 hr with 2 mM EDTA in phosphate buffered saline (PBS, minus divalent cations), from the second plate after 48 hr and from the third plate after 72 hr. The doubling time for C8161 cells in the presence of each compound was then determined and compared to the DMSO treated cells (control).

The effect of CMTs on the proliferation of C8161 cells on plastic is reported in Table 4, below:

TABLE 4

Effect of Tetracycline Compounds on C8161 Cell Proliferation

| Compound | Doubling Time |
|---|---|
| DMSO | 22 hr |
| CMT-1 | 24 hr |
| CMT-3 | 28 hr |
| CMT-4 | 22 hr |
| CMT-6 | 24 hr |
| CMT-7 | 24 hr |
| CMT-8 | 26 hr |
| Doxycycline | 22 hr |

EXAMPLE 8

Gelatin-Incorporated SDS-Polyacrylamide Gel Electrophoresis (Zymography)

Six hundred thousand ($6 \times 10^5$) C8161 cells were seeded per well in a 12-well dish coated with a laminin/collagen IV/gelatin matrix in DMEM plus Mito+ and 0.1% gentamicin sulfate. After approximately 1 hr incubation to allow the cells to attach, 50 µg/mL of either doxycycline or one of the other CMTs was added per well and the dish then placed in a 37° C. humidified 5% $CO_2$ incubator. After 24 hr, the supernatants were removed and centrifuged to remove any cells or debris. One volume of Laemmli sample buffer minus reductant was added to two volumes of the medium, and this sample electrophoresed without prior heating or boiling on a 10% SDS-PAGE containing 0.1% gelatin (samples normalized based on the same number of cells per volume of medium per time of incubation). After electrophoresis, the gels were washed with gentle shaking at room temperature for 30 min in 50 mM Tris-HCl (pH 7.5) plus 2.5% TRITON® X100 plus 50 µg/mL of the corresponding CMT used in the original treatment. The gel was then placed in incubation buffer (50 mM Tris-Cl/10 mM $CaCl_2$/150 mM NaCl/ 0.05% $NaN_3$) also containing 50 µg/mL of the corresponding CMT, and incubated at 37° C. for 20–24 hr. The gels were stained with Coomassie BBR-250, then destained with 10% methanol/10% acetic acid in water until the wash remained clear. A photographic negative of the gel was digitized using a video camera and Snappy Video Snapshot system (Play Inc., Rancho Cordova, Calif.). An integrated density was determined for each of the cleared zones of proteolysis using the software ImagePC8α (freely available from the National Institutes of Health), and the corresponding changes in gelatinolytic activities reported compared to the control samples normalized to a value of 1.0.

The relative amount of gelatinolytic enzyme activity in the conditioned medium from C8161 cells treated with these compounds was measured by zymography (data not shown), and quantified against the amount of activity in the control samples by densitometric analysis, as shown in Table 5, below:

TABLE 5

Densitometric Analysis of Zymograms

| Compound | Gelatinase A | Gelatinase B |
|---|---|---|
| Control | 1.00* | 1.00* |
| Doxycycline | 0.26 | 0.40 |
| CMT-1 | 0.24 | 0.22 |
| CMT-2 | 0.89 | 1.51 |
| CMT-3 | 0.22 | 0.03 |
| CMT-4 | 0.75 | 0.12 |
| CMT-6 | 0.07 | 0.51 |
| CMT-7 | 0.17 | 1.22 |
| CMT-8 | 0.70 | 1.05 |

*Integrated density of digitized photographic negative normalized to a value of 1.00 for the control samples using the image analysis software ImagePCα (NIH).

Treatment of C8161 cells with each of these compounds resulted in a decrease in extracellular levels of gelatinase A activity (Table 5), ranging from 11% to 93% (CMT-2<CMT-4<CMT-8<doxycycline<CMT-1<CMT-3<CMT-7<CMT-6). Cells treated with five of the compounds also resulted in a decrease in extracellular levels of gelatinase B, from 49% to 97% (CMT-6<doxycycline<CMT-1<CMT-4<CMT-3). Treatment with three of the CMTs resulted in an increase in extracellular levels of gelatinase B (5 to 51%; CMT-8<CMT-7<CMT-2).

EXAMPLE 9

In Vitro Invasion Assay

The in vitro invasive potentials of the control (DMSO only) and chemically-modified tetracycline treated cells were measured using a modified Boyden chamber as previously described (Membrane Invasion Culture System, MICS). An intervening barrier consisting of a polycarbonate filter containing 10 µm pores (Osmonics, Livermore, Calif.)

coated with a defined matrix of human laminin/collagen IV/gelatin (Sigma, St. Louis, Mo.) was used for these studies. C8161 human melanoma cells were seeded into the upper wells of the chamber in DMEM containing Mito+ (Collaborative Biomedical, Bedford, Mass.; i.e., serum-free medium) and allowed to attach at 37° C. in a humidified 5% $CO_2$ incubator. Doxycycline or individual CMTs were then added to different wells of the chamber at 3, 20 or 50 μg/mL 2 hr post-seeding and daily during the assay. After 48 hr, the cells were removed from the lower wells and the number of invasive cells was determined and compared to the original number of cells seeded into the upper wells. Where appropriate, data were corrected for proliferation during the period of the in vitro assay.

The effects of doxycycline and the CMTs at three different concentrations (range: 3 μg/mL; 20 μg/mL; 50 μg/mL) on the in vitro invasive potential of C8161 cells are shown in FIG. 8. These data are summarized in Table 6, below.

TABLE 6

Inhibition of Invasive Potential of C8161 Cells Through a Laminin/Collagen IV/Gelatin Matrix-Coated Filter

| Compound | Percent Inhibition | Type of Inhibition |
| --- | --- | --- |
| Doxycycline | 12–79% | dose dependent |
| CMT-1 | 26–58% | dose-dependent |
| CMT-2 | ~10% | non-dose dependent |
| CMT-3 | 35–74% | dose dependent |
| CMT-4 | ~20% | non-dose dependent |
| CMT-6 | 8–50% | dose dependent |
| CMT-7 | 15–55% | non dose-dependent |
| CMT-8 | ~12% | non-dose dependent | wrapped in aluminum foil to prevent any light induced changes, and each day's supply was thawed just prior to use.

Four compounds were tested for their effects on the metastatic potential of C8161 cells injected intravenously via the tail vein: CMT-1, CMT-3, and CMT-7 at 40 and 100 mg/kg, CMT-8 at 40 mg/kg, compared to the control. The concentration of the compounds in the vials used to give the 100 mg/kg doses were 2.5 times that in the 40 mg/kg dose so that approximately the same volume was used in both cases, approximately 0.5 mL/animal. The experiments started with nine animals per group at day −4. On day zero, $2 \times 10^5$ C8161 cells in cold Hank's Balanced Salt Solution (HBSS) were injected intravenously via tail vein inoculation. The experiment was continued for an additional 24 days, at which time the animals were sacrificed and their lungs removed and fixed in a solution of Bouins/formaldehyde (5 parts: 1 part). Tumors were quantitated on the entire surface of the lungs by rotating the lungs and counting the tumors on each lobe using a 6X magnifying glass. Statistical analysis was performed using the statistical package of Microsoft's Excel spreadsheet software.

The effects of CMT-1, CMT-3, CMT-7 and CMT-8, at two different concentrations, on the metastatic potential of C8161 cells in SCID mice are presented in Table 7, below:

TABLE 7

Effect of CMTs on the Metastatic Potential of C8161 Cells in SCID Mice

| Compound | Dosage | Number of Lung Metastases/Mouse* | Range | Number of Mice (n) | p value[†] |
| --- | --- | --- | --- | --- | --- |
| Control | 0.5 mL vehicle[‡] | 231 ± 49 | 120 to >250 | 7 | |
| CMT-1 | 40 mg/kg | 129 ± 102 | 3 to >250 | 9 | 0.023 |
| | 100 mg/kg | 240 ± 28 | 165 to >250 | 5 | 0.647 |
| CMT-3 | 40 mg/kg | 111 ± 105 | 4 to >250 | 9 | 0.033 |
| | 100 mg/kg | 176 ± 82 | 9 to >250 | 5 | 0.141 |
| CMT-7 | 40 mg/kg | 136 ± 107 | 63 to >250 | 6 | 0.169 |
| | 100 mg/kg | 166 ± 101 | 11 to >250 | 5 | 0.157 |
| CMT-8 | 40 mg/kg | 186 ± 60 | 124 to >250 | 7 | 0.184 |
| | 100 mg/kg | | (see note below) | | |

*Average ± SEM.
[†]p < 0.05 compared to control is considered a significant difference.
[‡]Sterile water containing 2% carboxymethyl cellulose.
Note:
This group of mice was the first to be treated by gavage, and did not survive due to technical difficulties.

EXAMPLE 10
In Vivo Metastasis Assay

Immunosuppressed mice (athymic nude/nude SCID females from Harlan Sprague Dawley) were housed in autoclaved cages with microisolator tops, and all manipulations of the animals were done in a laminar flow hood after wiping down both the hood, gloves and cages with ABQ sterilant. The mice were fed sterile Pico Lab Chow (Purina) and autoclaved St. Louis tap water. Doxycycline or the CMTs were administered intra-gastrically daily to the mice in sterile water containing 2% carboxymethyl cellulose via sterile, disposable animal feeding needles (Poper & Sons Cat #9921; 20 g×1.5"), seven days a week between 7:00 and 8:00 am. The compounds and control (sterile water plus 2% carboxymethyl cellulose) were kept stored at −80° C.

Oral gavaging of the animals with CMT-1 or CMT-3 significantly reduced the number of lung metastases in the SCID mouse population when administered daily at 40 mg/kg (p<0.05), but did not significantly reduce the number of lung metastases at the 100 mg/kg dosage. The compounds CMT-7 and CMT-8 did not significantly reduce the number of lung metastases at either dosage (p>0.05).

EXAMPLE 11
Differential Cytotoxicity of Tetracycline Compounds Against Cancer Cells Several cancer cell lines and normal cells were examined in vitro to determine whether tetracycline compounds produce cytotoxic (cell killing) effects. A conventional assay for viability of cultured cells based on redox activity in the cells was employed (Pagé et al. 1993). The assay uses a redox dye Alamar Blue, which is a fluorogenic indicator dye that is converted to a fluorescent red product only when cells are carrying out electron transport activity, a widely accepted criterion of viability.

Cultured cells from three prostate tumor cell lines, LNCAP, DU-145, and PC-3, and normal prostate stromal cells obtained by biopsy of a normal 37-year old man, were allowed to grow to confluence in multiwell microplates to minimize differences in proliferative activity among the cell types at the time of exposure to the test compound. CMT-3 was added to the wells at concentrations of 10 μM and 20 μM (50 μM also in the case of DU-145). At the start of the experiment, and again at 1, 2, and 3 days, selected wells were incubated with the indicator dye for 3 hr, and the fluorescence was measured on a Cytofluor 2300 fluorescent microplate reader. The results are summarized in FIGS. 9A–9D.

Normal prostate stromal cells showed virtually no change in fluorescence over the three-day period, regardless of CMT-3 dose (FIG. 9A). A slight increase on day 1 in the stromal cells not exposed to CMT-3 supported our intention to avoid introducing the complication of marked differences in proliferative activity among the different cell being studied. LNCAP cells proved to be exquisitely sensitive to CMT-3 even under these conditions of limited proliferative activity: cytotoxicity is complete within 24 hr at 20 μM, and nearly complete at that time in 10 μM CMT-3 (FIG. 9B). PC-3 tumor cells are somewhat less susceptible to CMT-3, which induces about 25% cytotoxicity at 24 hr, 50% at 48 hr and 75% after 72 hr (FIG. 9C). DU-145 tumor cells are less sensitive, with some cytotoxicity appearing after 72 hr at 20 μM (FIG. 9D). DU-145 cells show significant cytotoxicity at 50 μM, which gradually develops over the course of the 72 hr test period. Normal cells exposed to 50 μM CMT-3 show no comparable cytotoxicity (data not shown).

It is to be noted that marked differences in cellular morphology were observed between the normal stromal cells and the tumor cells after exposure to CMT-3: no significant changes could be seen in the normal stromal cells, whereas all of the tumor cell types became progressively vacuolated.

EXAMPLE 12
Cytotoxicity of Tetracycline Compounds Against Cancer Cells

A panel of chemically modified tetracycline compounds and doxycycline were tested for cytotoxicity against two carcinomas: COLO 205 (a human colon carcinoma-derived cell line) and the E-10 clone of MDA-MB-231 (a human breast carcinoma-derived cell line). Cytotoxicity was measured using a conventional assay for viability with a tetrazolium salt (MTS). Cells were grown in media containing the CMTs at concentrations ranging from 5 μM to 100 μM for two days. The cells were then incubated with the MTS for several hours before removal of the supernatant medium for determination of formazan, which is generated only by the viable cells. The results are presented in Tables 8A and 8B below. Results are expressed as percent cytotoxicity, which is simply the percent decline in measured formazan concentration in the sampled medium. Two different lots of CMT-3 were tested, designated "A" and "B".

TABLE 8A

Cytotoxic Effect of CMTs on COLO 205 Cells In Vitro

| Compound | 5 μM | 10 μM | 20 μM | 50 μM | 100 μM |
|---|---|---|---|---|---|
| CMT-1 | 0 | 4 | 32.5 | 63.8 | 82.8 |
| CMT-2 | 2.7 | 4.5 | 0 | 7 | 16.3 |
| CMT-3 | 17 | 28.8 | 52 | 79 | 85.6 |

TABLE 8A-continued

Cytotoxic Effect of CMTs on COLO 205 Cells In Vitro

| Compound | 5 μM | 10 μM | 20 μM | 50 μM | 100 μM |
|---|---|---|---|---|---|
| CMT-3 | 25.9 | 38.9 | 37 | 86.7 | 86.7 |
| CMT-4 | 1.8 | 6.8 | 25.3 | 73.3 | 81.9 |
| CMT-5 | 0 | 0 | 0 | 0 | 0 |
| CMT-6 | 1.7 | 0 | 0 | 0 | 22.2 |
| CMT-7 | 0 | 0 | 0 | 0 | 29.4 |
| CMT-8 | 0 | 20.5 | 35.5 | 44.4 | 50 |
| Doxycycline | 0 | 0 | 45.7 | 58.8 | 66.5 |

TABLE 8B

Cytotoxic Effect of CMTs on E-10 Cells In Vitro

| Compound | 5 μM | 10 μM | 20 μM | 50 μM | 100 μM |
|---|---|---|---|---|---|
| CMT-1 | 7.6 | 0 | 0 | 2.2 | 7.6 |
| CMT-2 | 1.5 | 3.8 | 0.8 | 0 | 2.3 |
| CMT-3 | 0 | 0 | 4.15 | 3 | 13.9 |
| CMT-3 | 0 | 1.8 | 8.5 | 17.7 | 47 |
| CMT-4 | 9 | 16.7 | 0.8 | 0 | 0 |
| CMT-5 | 0 | 0 | 0 | 0 | 0 |
| CMT-6 | 0 | 6 | 3 | 7.6 | 16.7 |
| CMT-7 | 0 | 0 | 0 | 0 | 8.3 |
| CMT-8 | 0 | 0 | 0 | 0 | 0 |
| Doxycycline | 0 | 0 | 4.5 | 24.2 | 29.5 |

EXAMPLE 13
Cytotoxicity of Tetracycline Compounds Against Cancer Cells

An investigation of the cytotoxicity of chemically modified tetracycline compounds for cancer cells was undertaken to determine involvement of programmed cell death (apoptosis) (see Duke et al. 1986). MAT LyLu cells were incubated with various concentration of CMT-3 and doxycycline. Conditioned media were assayed for soluble nucleosomes, resulting from internucleosomal DNA strand breaks, using the Cell Death Detection ELISA Plus kit from Boehringer Mannheim GmbH (Catalog No. 1774425) according to the manufacturer's instructions. In the dosage-dependence trials, cells were incubated with the tetracycline compounds for 48 hr, and then media were collected. In the time trials, the cells were exposed to the tetracycline compounds for specific periods of time from 0 to 48 hr, and if appropriate were maintained in fresh media until 48 hr from the start of the experiment at which time media were collected. The experiments were performed three times, and representative data are shown in FIGS. 10A and 10B.

As shown in FIG. 10A, a dose-dependent increase in soluble nucleosomes was observed in the MAT LyLu cells treated with CMT-3, but not in the cells treated with doxycycline. In fact, programmed cell death induction was insignificant even at a doxycycline concentration exceeding the 50% growth inhibiting dose ($GI_{50}$) as determined by proliferation assays as described above. The amount of soluble nucleosomes released into the media was directly proportional to the fractions of apoptotic cells, as determined microscopically in select cases. Furthermore, as shown in FIG. 10B, a brief period of exposure to CMT-3 (4 hr at 5 μg/mL or 10 μg/mL) was sufficient to elicit a putative programmed cell death response in the MAT LyLu cells, but no such response was observed for the doxycycline-treated cells (data not shown).

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

BIBLIOGRAPHY

The following publications, having been mentioned in the foregoing specification, are incorporated herein by reference for all that they disclose:

Albini A, Iwamoto Y, Kleinman H K, Martin G R, Aaronson S A, Kozlowski J M, and McEwan R M, "A rapid in vitro assay for quantitating the invasive potential of tumor cells," Cancer Res 47:3239–3245 (1987), Dean D D and Woessner J F Jr, "A sensitive, specific assay for tissue collagenases using telopeptide-free $^3$H-acetylated collagen," Anal Biochem 148:174–181 (1985).

Dean D D, Curry T E, LeMaire W J, and Woessner J F Jr, "Determination of metalloproteinase activity after selective destruction of tissue inhibitor of metalloproteinases," Trans 33rd Mtg Orthopedic Res Soc, 12:248 (1987).

DeClerck Y A, Shimada H, Taylor S M, and Langley K E, "Matrix metalloproteinases and their inhibitors in tumor progression," Annals NY Acad Sci 732:222–232 (1994).

Dudak S D, Lopez A, Block N L, and Lokeshwar B L, "Enhancement of radiation response of prostatic carcinoma by lonidamine," Anticancer Res 16:3665–3672 (1996).

Duke R C and Cohen J J, "IL-2 addiction: withdrawal of growth factor activates a suicide program in dependent T cells,: Lymphokine Res 5:289–299 (1986).

Emmert-Buck M R, Roth M J, Zhuang Z, Campo E, Rozhin J, Sloane B F, Liotta L A, and Stetler-Stevenson W, "Increased gelatinase A (MMP-2) and cathepsin B activity in invasive tumor regions of human colon cancer samples," Am J Pathol 145(6):1285–1290 (1994).

Golub L M, Ramamurthy N S, and McNamara T F, Crit Rev Oral Biol Med 2:297–322 (1991).

Golub L M, Sorsa T, and Suomalainen K, Curr Opin Dent 2:80–90 (1992).

Greenwald R A, Moak S A, Ramamurthy N S, and Golub L M, "Tetracyclines suppress matrix metalloproteinase activity in adjuvant arthritis and in combination with flurbiprofen, ameliorate bone damage," J Rheumatol 19:927–938 (1992).

Hayward S W, Dahiya R, Cunha G R, Bartek J, Deshpande N, and Narayan P, "Establishment and characterization of an immortalized but non-transformed human prostate epithelial cell line: BPH-1," In Vitro Cell Dev Biol Anim 31(1):14–24 (1995).

Kroon A M, Dontje B H J, Holtrop M, and van den Bogert C, "The mitochondrial genetic system as a target for chemotherapy: tetracyclines as cytostatics," Cancer Letts 25(1):33–40 (1984).

Lokeshwar B L, Selzer M G, Block N L, and Gunja-Smith Z, "Secretion of matrix metalloproteinases and the inhibitors (TIMPs) by human prostate in explant cultures: Reduced tissue inhibitor of metalloproteinase secretion by malignant tissues," Cancer Res 53:4493–4498 (1993a).

Lokeshwar B L, Hurkadli K S, Sheth A R, and Block N L, "Human prostatic inhibin suppresses tumor growth and inhibits clonogenic cell survival of a model prostatic adenocarcinoma, the Dunning R3327G rat tumor," Cancer Res 53:4855–4859 (1993b).

Lokeshwar B L, Ferrell S M, and Block N L, "Radiation sensitization of prostatic adenocarcinoma by taxol: Potential for therapeutic application in advanced malignancy," Anticancer Res 15:93–98 (1995a).

Lokeshwar B L, Lokeshwar V B, and Block N L, "Expression of CD44 in prostate cancer cells: Association with cell proliferation and invasive potential," Anticancer Res 15:1191–1198 (1995b).

Lokeshwar B, Dudak S, Selzer M, Block N, and Golub L, "Novel therapies for metastatic prostate cancer: Chemically modified tetracycline," in Therapeutic Strategies in Molecular Medicine, Miami Biotechnoloy Short Report Vol. 7: Advances in Gene Technology, Oxford University Press, London (1996).

Maragoudakis M E, Peristeris P, Missirlis E, Aletras A, Andriopoulou P, and Haralabopoulos G, Annals NY Acad Sci 732:280–293 (1994).

Mitscher L A, The Chemisty of the Tetracycline Antihiotics, Ch. 6, Marcel Dekker, New York (1978).

Nip L H, Uitto V-J, and Golub L M, "Inhibition of epithelial cell matrix metalloproteinases by tetracyclines," J Periodont Res 28:379–385 (1993).

Pagé B, Pagé M, and Noël C, "A new fluorometric assay for cytotoxicity measurements in vitro," International J Oncol 3.:473–476 (1993).

Rifkin B R, Vernillo A T, and Golub L M, "Blocking periodontal disease progression by inhibiting tissue-destructive enzymes: a potential therapeutic role for tetracyclines and their chemically-modified analogs," Amer Acad Periodontol 64:819–827 (1993).

Seftor R E B, Seftor E A, Gehlsen K R, Stetler-Stevenson W G, Brown P D, Ruoslahti E, and Hendrix M J C, "Role of the $\alpha_v\beta_3$ integrin in human melanoma cell invasion," Proc Natl Acad Sci USA 89:1557–1561 (1992).

Seftor R E B, Seftor E A, Stetler-Stevenson W G, and Hendrix M J C, "The 72 kDa type IV collagenase is modulated via differential expression of $\alpha_v\beta_3$ and $\alpha_5\beta_1$ integrins during human melanoma cell invasion," Cancer Res 53:3411–3415 (1993).

Sorsa T, Konttinen Y T, Lindy O, Suomalainen K, Ingman T, Saari H, Halinen S, Lee H-M, Golub L M, Hall J, and Simon S, "Doxycycline protects serum alpha-1-antitrypsin from human neutrophil collagenase," Agents Actions Suppl 39:225–229 (1993).

Uitto V J, Firth J D, Nip L, and Golub L M, "Doxycycline and chemically modified tetracyclines inhibit gelatinase A (MMP-2) gene expression in human skin keratinocytes," Annals NY Acad Sci 732:140–151 (1994).

van den Bogert C, Dontje B H J, Holtrop M, Melis T E, Romijn J C, van Dongen J W, and Kroon A M, "Arrest of the proliferation of renal and prostate carcinomas of human origin by inhibition of mitochondrial protein synthesis," Cancer Res 46(7):3283–3289 (1986).

Woessner J F Jr., "Matrix metalloproteinases and their inhibitors in connective tissue remodeling," FASEB J 5:2145–2154 (1991).

Yamamoto M, Mohanam S, Sawaya R, Fuller G N, Seiki M, Sato H, Gokaslan Z L, Liotta L A, Nicolson G L, and Rao J S, "Differential expression of membrane-type matrix metalloproteinase and its correlation with gelatinase A activation in human malignant brain tumors in vivo and in vitro," Cancer Res 56(2):384–392 (1996).

Yu Z, Leung M K, Ramamurthy N S, McNamara T F, and Golub L M, "HPLC determination of a chemically modified nonantimicrobial tetracycline: Biological implications," Biochem Medicine Metab Biol 47:10–20 (1992).

Zucker S, Lysick R M, Ramamurthy N S, Golub L M, Wieman J M, and Wilkie D P, "Diversity of plasma membrane proteinases in mouse melanoma cells: Inhibition of collagenolytic activity and cytolytic activity by minocycline," J Natl Cancer Inst 75:517–525 (1985).

What is claimed is:

1. A method of inhibiting cancer growth in a mammal, comprising administering to the mammal a cancer-inhibitory amount of a tetracycline compound selected from the group consisting of:

4-de(dimethylamino)tetracycline (CMT-1), 4-de(dimethylamino)-7-chlorotetracycline (CMT-4), 4-hydroxy-4-de(dimethylamino)tetracycline (CMT-6), 4-de(dimethylamino)-12α-deoxytetracycline (CMT-7), and 6α-deoxy-5-hydroxy-4-de(dimethylamino)tetracycline (CMT-8);

wherein said cancer is selected from the group consisting of prostate, breast, colon, lung melanoma and lymph cancers.

2. A method according to claim 1, wherein the cancer is a carcinoma.

3. A method according to claim 2, wherein the cancer is an adenocarcinoma.

4. A method according to claim 3, where in the cancer is an adenocarcinoma of the lung, prostate, breast, testes, or colon.

5. A method according to claim 1, wherein the cancer is a melanoma.

6. A method according to claim 1, wherein the method comprises inhibiting cellular proliferation of the cancer.

7. A method according to claim 1, wherein the method comprises inhibiting invasiveness of the cancer.

8. A method according to claim 1, wherein the method comprises inhibiting metastasis of the cancer.

9. A method according to claim 1, wherein the tetracycline compound is administered in an amount sufficient to specifically inhibit expression of a matrix metalloproteinase by cells of the cancer.

10. A method according to claim 9, wherein the matrix metalloproteinase is a gelatinase.

11. A method according to claim 10, wherein the matrix metalloproteinase is gelatinase A or gelatinase B.

12. A method according to claim 1, further comprising treating the mammal with an adjunct antineoplastic modality.

13. A method according to claim 12, wherein the adjunct antineoplastic modality comprises chemotherapy, surgery, or radiotherapy.

14. A method of inhibiting proliferation of cancer cells, comprising contacting the cancer cells with a proliferation-inhibitory amount of a tetracycline compound selected from the group consisting of:
6-α-deoxy-5-hydroxy-4-de(dimethylamino)tetracycline (CMT-8),
4-de(dimethylamino)tetracycline (CMT-1),
4-hydroxy-4-de(dimethylamino)tetracycline (CMT-6), and
4-de(dimethylamino)-12α-deoxytetracycline (CMT-7);
wherein said cancer is selected from the group consisting of prostate, breast, colon, lung melanoma and lymph cancers.

15. A method according to claim 14, wherein the tetracycline compound is 6-α-deoxy-5-hydroxy-4-de(dimethylamino)tetracycline (CMT-8).

16. A method of inhibiting the invasive potential of cancer cells, comprising contacting the cancer cells with an invasion-inhibitory amount of a tetracycline compound selected from the group consisting of:
4-de(dimethylamino)tetracycline (CMT-1),
4-de(dimethylamino)-12α-deoxytetracycline (CMT-7),
4-hydroxy-4-de(dimethylamino)tetracycline (CMT-6),
4-de(dimethylamino)-7-chlorotetracycline (CMT-4),
6-α-deoxy-5-hydroxy-4-de(dimethylamino)tetracycline (CMT-8), and
tetracyclinonitrile (CMT-2);
wherein said cancer is selected from the group consisting of prostate, breast, colon, lung melanoma and lymph cancers.

17. A method of inhibiting the metastatic potential of cancer cells, comprising contacting the cancer cells with a metastasis-inhibitory amount of
4-de(dimethylamino)tetracycline (CMT-1);
wherein said cancer is selected from the group consisting of prostate, breast, colon, lung melanoma and lymph cancers.

18. A method of treating a cancer condition characterized by excessive gelatinolytic activity, comprising administering to a mammal an amount of a tetracycline compound effective to inhibit excessive gelatinolytic activity;
wherein the tetracycline compound is selected from the group consisting of:
4-hydroxy-4-de(dimethylamino)tetracycline (CMT-6),
4-de(dimethylamino)-12α-deoxytetracycline (CMT-7),
4-de(dimethylamino)tetracycline (CMT-1),
6-α-deoxy-5-hydroxy-4-de(dimethylamino)tetracycline (CM-8),
4-de(dimethylamino)-7-chlorotetracycline (CMT-4), and
tetracyclinonitrile (CMT-2).

19. A method according to claim 18, wherein the excessive gelatinolytic activity is characterized by excessive activity of gelatinase A.

20. A method according to claim 19, wherein the tetracycline compound is
4-hydroxy-4-de(dimethylamino)tetracycline (CMT-6) or
4-de(dimethylamino)-12α-deoxytetracycline (CMT-7).

21. A method according to claim 18, wherein the cancer condition is characterized by excessive activity of gelatinase B, and the tetracycline compound is selected from the group consisting of:
4-de(dimethylamino)-7-chlorotetracycline (CMT-4),
4-de(dimethylamino)tetracycline (CMT-1), and
4-hydroxy-4-de(dimethylamino)tetracycline (CMT-6).

22. A method according to claim 21, wherein the tetracycline compound is 4-de(dimethylamino)-7-chlorotetracycline (CMT-4).

23. A method of inhibiting tumor incidence in a mammal, comprising
(a) detecting in a biological sample from the mammal a gene product or metabolite associated with predisposition to a cancer prior to observing any specific cancerous lesion; and
(b) administering to the mammal a tumor incidence-inhibiting amount of a tetracycline compound selected from the group consisting of:
4-de(dimethylamino)tetracycline (CMT-1),
tetracyclinonitrile (CMT-2),
4-de(dimethylamino)-7-chlorotetracycline (CMT-4), and
4-hydroxy-4-de(dimethylamino)tetracycline (CMT-6),
4-de(dimethylamino)-12α-deoxytetracycline (CMT-7) and
6-α-deoxy-5-hydroxy-4-de(dimethylamino)tetracycline (CMT-8);
wherein said cancer is selected from the group consisting of prostate, breast, colon, lung melanoma and lymph cancers.

24. A method of inhibiting gelatinolytic activity associated with a cancerous tumor in a mammal, comprising administering to the mammal an amount of a tetracycline compound effective to inhibit gelatinolytic activity;
wherein the tetracycline compound is selected from the group consisting of:
4-hydroxy-4-de(dimethylamino)tetracycline (CMT-6),
4-de(dimethylamino)-12α-deoxytetracycline (CMT-7),
4-de(dimethylamino)tetracycline (CMT-1),
6-α-deoxy-5-hydroxy-4-de(dimethylamino)tetracycline (CMT-8),
4-de(dimethylamino)-7-chlorotetracycline (CMT-4),
and tetracyclinonitrile (CMT-2);
wherein said cancer is selected from the group consisting of prostate, breast, colon, lung melanoma and lymph cancers.

25. A method according to claim 24, wherein the gelatinolyic activity derives from the cancerous tumor.

26. A method according to claim 24, wherein the gelatinolyic activity derives from normal tissue.

27. A method according to claim 26, wherein the normal tissue is epithelial tissue.

28. A method according to claim 24, wherein the normal tissue is stromal tissue.

29. A method of inhibiting cancer growth in a mammal, comprising topically administering to the mammal a cancer-inhibitory amount of 4-hydroxy-4-de(dimethylamino)tetracycline (CMT-6).

30. A method of differentially killing cancer cells, comprising contacting cancer cells with a cytotoxic amount of a tetracycline compound selected from the group consisting of:

4-de(dimethylamino)tetracycline (CMT-1), 4-de(dimethylamino)-7-chlorotetracycline (CMT-4), 4-hydroxy-4-de(dimethylamino)tetracycline (CMT-6), 4-de(dimethylamino)-12α-deoxytetracycline (CMT-7) and 6-α-deoxy-5-hydroxy-4-de(dimethylamino)tetracycline (CMT-8);

wherein said cancer is selected from the group consisting of prostate, breast, colon, lung, melanoma and lymph cancers.

31. A method according to claim 30, wherein the cancer cells are cells of a sarcoma, a carcinoma, or an adenocarcinoma.

32. A method according to claim 31, wherein the cancer cells are cells of a carcinoma of the prostate, testis, lung, colon, or breast.

33. A method of inhibiting the growth of a cancer in a mammal, comprising administering to a mammal having a cancer an amount of a tetracycline compound sufficient to induce cytotoxicity in cells of the cancer, wherein the tetracycline compound is selected from the group consisting of:

4-de(dimethylamino)tetracycline (CMT-1), 4-de(dimethylamino)-7-chlorotetracycline (CMT-4), 4-hydroxy-4-de(dimethylamino)tetracycline (CMT-6), 4-de(dimethylamino)-12α-deoxytetracycline (CMT-7), and 6-α-deoxy-5-hydroxy-4-de(dimethylamino)tetracycline (CM-8);

wherein said cancer is selected from the group consisting of prostate, breast, colon, lung and lymph cancers.

34. A method of inhibiting melanoma growth in a mammal, comprising administering to the mammal a cancer-inhibitory amount of tetracyclinonitrile (CMT-2) or 6-demethyl-6-deoxy-4-de(dimethylamino)tetracycline (CMT-3).

* * * * *

UNITED STATES PATENT AND TRADEMARK OFFICE
CERTIFICATE OF CORRECTION

PATENT NO. : 6,100,248

DATED : August 8, 2000

INVENTOR(S) : Golub et al.

Page 1 of 2

It is certified that error appears in the above-indentified patent and that said Letters Patent is hereby corrected as shown below:

In Column 21, Line 45, The text following Table 4 prior to Example 8 was omitted. The following text should be inserted: --As shown, CMT-4 and doxycycline did not affect the doubling time of C8161 cells on plastic; CMT-1, CMT-6 and CMT-7 slightly increased the doubling time of the cells (approximately 9%), and CMT-8 and CMT-3 increased the doubling time by approximately 18% and 27%, respectively.--

UNITED STATES PATENT AND TRADEMARK OFFICE
CERTIFICATE OF CORRECTION

PATENT NO. : 6,100,248
DATED : August 8, 2000
INVENTOR(S) : Golub et al.

It is certified that error appears in the above-indentified patent and that said Letters Patent is hereby corrected as shown below:

<u>In Column 26, Line 28,</u> The text following Table 8B prior to Example 13 was omitted. The following text should be inserted: --The above data shows that CMT-3 is the most potent of the tested compounds, with CMT-1, CMT-4 and CMT-8 also producing significant cytotoxicity. Doxycyline also produced some cytotoxicity.--

Signed and Sealed this

Seventeenth Day of April, 2001

Attest:

NICHOLAS P. GODICI

*Attesting Officer*     *Acting Director of the United States Patent and Trademark Office*

UNITED STATES PATENT AND TRADEMARK OFFICE
CERTIFICATE OF CORRECTION

PATENT NO. : 6,100,248
DATED : August 8, 2000
INVENTOR(S) : Golub et al.

It is certified that error appears in the above-identified patent and that said Letters Patent is hereby corrected as shown below:

Column 1,
Lines 7-12, now reads "This invention was made with Government support under Grant No. R37-DE03987 awarded by the National Institutes of Health through the National Institute of Dental Research and Grant No. R29-CA61038 awarded by the National Institutes of Health. The Government has certain rights in the invention." should read -- This invention was made with Government support under Grant No. R37-DE03987 awarded by the National Institutes of Health through the National Institute of Dental Research; Grant No. R29-CA61038 awarded by the National Institutes of Health; and Grant No. DAMD179818560 awarded by the United States Army Medical Research Acquisition Activity. The Government has certain rights in the invention. --

Signed and Sealed this

Ninth Day of April, 2002

Attest:

Attesting Officer

JAMES E. ROGAN
Director of the United States Patent and Trademark Office